United States Patent
Natarajan et al.

(10) Patent No.: US 11,104,684 B2
(45) Date of Patent: Aug. 31, 2021

(54) DIMERS OF COVALENT NFKB INHIBITORS

(71) Applicant: BOARD OF REGENTS OF THE UNIVERSITY OF NEBRASKA, Lincoln, NE (US)

(72) Inventors: Amarnath Natarajan, Elkhorn, NE (US); Sandeep Rana, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 16/471,070

(22) PCT Filed: Dec. 21, 2017

(86) PCT No.: PCT/US2017/067794
§ 371 (c)(1),
(2) Date: Jun. 19, 2019

(87) PCT Pub. No.: WO2018/119177
PCT Pub. Date: Jun. 28, 2018

(65) Prior Publication Data
US 2019/0322680 A1  Oct. 24, 2019

Related U.S. Application Data

(60) Provisional application No. 62/437,087, filed on Dec. 21, 2016.

(51) Int. Cl.
| | | |
|---|---|---|
| *C07D 487/10* | (2006.01) | |
| *C07D 491/107* | (2006.01) | |
| *A61P 35/00* | (2006.01) | |
| *C07D 519/00* | (2006.01) | |

(52) U.S. Cl.
CPC .......... *C07D 491/107* (2013.01); *A61P 35/00* (2018.01); *C07D 487/10* (2013.01); *C07D 519/00* (2013.01)

(58) Field of Classification Search
CPC ..................... C07D 487/10; C07D 491/107
See application file for complete search history.

(56) References Cited

U.S. PATENT DOCUMENTS

| 5,466,468 A | 11/1995 | Schneider et al. |
| 2012/0289494 A1 | 11/2012 | Wang et al. |

FOREIGN PATENT DOCUMENTS

| WO | WO-2015/189799 A1 | 12/2015 |
| WO | WO-2016/195977 A1 | 12/2016 |

OTHER PUBLICATIONS

Chemical Abstracts Registry No. 1426259-25-7, indexed in the Registry file on STN CAS Online Mar. 25, 2013. (Year: 2013).*
PubChem CID 102113660, National Center for Biotechnology Information. "PubChem Compound Summary for CID 102113660" PubChem, https://pubchem.ncbi.nlm.nih.gov/compound/102113660. Accessed Sep. 15, 2020, create date Dec. 24, 2015. (Year: 2015).*
Khanna et al., ARKIVOC (Gainesville, FL, United States) (2009), (7), pp. 119-125. (Year: 2009).*
Fan et al., Advanced Synthesis & Catalysis (published online Dec. 21, 2016), 359(1), pp. 49-57. (Year: 2016).*
Berge et al., Pharmaceutical Salts, J. Pharm. Sci., 66(1):1-19 (1977).
Davis et al., Preparation and characterization of antibodies with specificity for the amino-terminal tetrapeptide sequence of the platelet-derived connective tissue activating peptide-III, Biochem. Int., 10(3):395-404 (Mar. 1985).
International Application No. PCT/US17/67794, International Preliminary Report on Patentability, dated Jun. 25, 2019.
International Application No. PCT/US17/67794, International Search Report and Written Opinion, dated Mar. 6, 2018.
Larsen et al., The Merrifield peptide synthesis studied by near-infrared Fourier-transform Raman spectroscopy, J. Am. Chem. Soc., 115:6247 (1993).
Merrifield et al., Solid phase peptide synthesis. I. The synthesis of a tetrapeptide, J. Am. Chem. Soc. 85: 2149 (1963).
O'Donnell et al., Solid-Phase Unnatural Peptide Synthesis (UPS), J. Am. Chem. Soc., 118(25):6070-1 (1996).
Pubchem CID 102113660, create date: Dec. 24, 2015; date accessed: Feb. 14, 2018.
Smith et al., Solid-phase peptide synthesis and biological activity of bovine thymopoietin II (bTP-II), Int. J. Pept. Protein Res., 44(2):183-91 (1994).
Stewart et al., Solid Phase Peptide Synthesis, Freeman (1969), Table of Contents Only.

* cited by examiner

*Primary Examiner* — Laura L Stockton
(74) *Attorney, Agent, or Firm* — Marshall, Gerstein & Borun LLP

(57) ABSTRACT

Provided herein are compounds and methods for modulating the NFκB pathway. More particularly, provided are inhibitors of the NFκB pathway and the uses of such inhibitors in regulating diseases and disorders, e.g., to treat cancer, autoimmune diseases, inflammatory diseases, diabetes, cardiovascular diseases, or neurological diseases.

20 Claims, 3 Drawing Sheets

DIMERS OF COVALENT NFKB INHIBITORS

STATEMENT OF U.S. GOVERNMENT SUPPORT

This invention was made with government support under grant numbers R21 CA182820 and R01CA197999 awarded by the National Institutes of Health. The government has certain rights in the invention.

BACKGROUND

Nuclear localization of the transcription factor NFκB has been implicated in oncogenesis and drug resistance in a number of cancers. Inhibition of the nuclear translocation of NFκB is hypothesized to be a viable therapeutic approach for cancer, and as such, the development of drugs providing novel approaches to inhibiting nuclear localization of NFκB is becoming an important strategy in addressing the need for additional therapies for the treatment of these disorders.

SUMMARY

The disclosure provides compounds of Formula I:

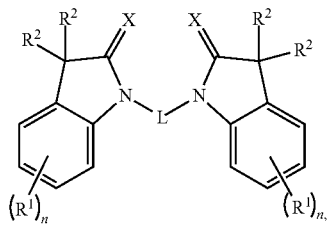

(I)

wherein X is O, S, or $NR^4$;

L is $C_{1-18}$alkylene or $C_{2-18}$alkenylene optionally interrupted with one or more of (i) non-adjacent heteroatom(s) selected from O, S, and $NR^4$, (ii) $C(O)NR^4$, (iii) $C_{6-10}$ aryl, (iv) 5-10 membered heteroaryl having 1-4 heteroatoms selected from N, O, and S, (v) 3-12 membered cycloalkyl ring, and (vi) 3-7 membered heterocycloalkyl ring having 1-3 ring heteroatoms selected from O, S, and N, and said aryl, heteroaryl, cycloalkyl, and heterocycloalkyl are optionally substituted with one or more $R^4$;

each $R^1$ is independently selected from the group consisting of $C_{1-6}$ alkyl, halo, CN, $N(R^4)_2$, $OR^4$, $NO_2$, $CO_2R^4$, $(C=O)R^4$, $CON(R^4)_2$, $NR^4(C=O)R^5$, $C_{6-10}$ aryl, and 5-10 membered heteroaryl having 1-4 heteroatoms selected from N, O, and S, and said alkyl can be optionally substituted with 1 to 3 $R^3$;

each $R^2$ is independently selected from the group consisting of $C_{1-6}$ alkyl, $C_{2-6}$ alkenyl, $C_{2-6}$ alkynyl, halo, $OR^4$, $COR^4$, $CO_2R^4$, $CON(R^4)_2$, $N(R^4)_2$, and $SR^4$, or a pair of two $R^2$ together with the carbon atom to which they are attached form a saturated or unsaturated 4-8 membered cycloalkyl or heterocycloalkyl ring, wherein the heterocycloalkyl ring has 1 or 2 ring heteroatoms selected from O, S, and N, and wherein said alkyl, alkenyl, alkynyl, cycloalkyl ring, and heterocycloalkyl ring are optionally substituted with 1 to 3 $R^3$, with the proviso that at least one $R^2$ or one pair of two $R^2$ together forming a ring comprise an α,β-unsaturated moiety;

each $R^3$ is independently selected from the group consisting of $C_{1-6}$ alkyl, $C_{2-6}$ alkenyl, $C_{2-6}$ alkynyl, halo, CN, $N(R^4)_2$, $OR^4$, $NO_2$, oxo, $=S$, $=NR^4$, $CO_2R^4$, $(C=O)R^4$, $CON(R^4)_2$, $C_{6-10}$ aryl, and 5-10 membered heteroaryl having 1-4 ring heteroatoms selected from N, O, and S, and wherein said alkyl, alkenyl, and alkynyl are optionally substituted with 1 to 3 $R^4$;

each $R^4$ is independently selected from the group consisting of H, $C_{1-6}$ alkyl, $C_{2-6}$ alkenyl, and $C_{2-6}$ alkynyl, wherein said alkyl, alkenyl, and alkynyl are optionally substituted with one or more substituents selected from the group consisting of halo, CN, $NH_2$, OH, and $C_{1-6}$ alkoxy; and n is 0-4.

In some embodiments, at least one pair of two $R^2$ together with the carbon atom to which they are attached form a ring having the structure:

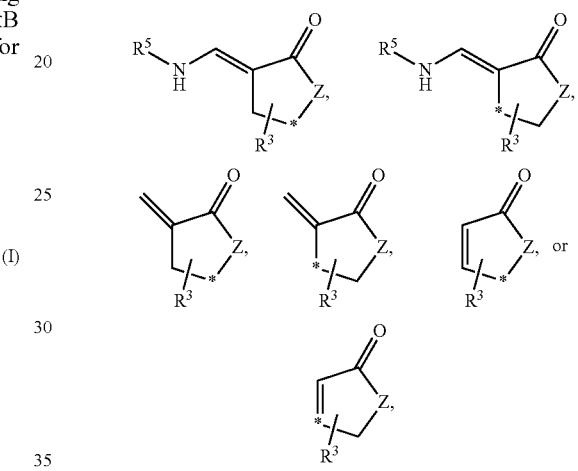

wherein * is the carbon atom to which each $R^2$ is attached, Z is O or $NR^4$, and $R^5$ is $C_{1-6}$alkyl, $C_{2-6}$alkenyl, $C_{6-10}$ aryl, or 3-7 membered heterocycloalkyl ring having 1-3 ring heteroatoms selected from O, S, and N.

In various embodiments, L is selected from the group consisting of uninterrupted $C_{1-18}$alkylene,

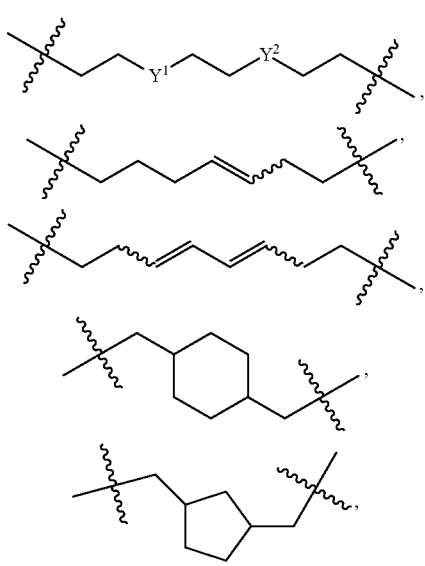

-continued

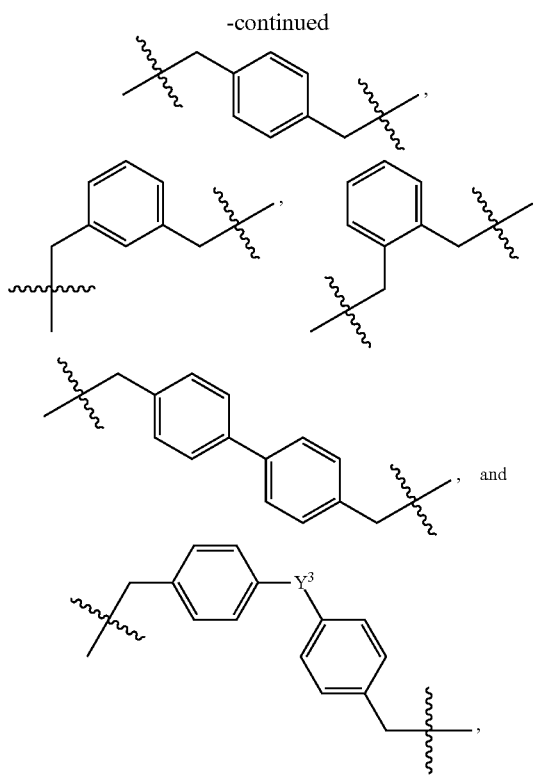

and $Y^1$, $Y^2$, and $Y^3$ are each independently O or $NR^4$, and ~~~ indicates that the double bond is cis or trans.

Further provided herein are methods of using the compounds to inhibit the NFκB pathway. Also provided are methods of treating or preventing a disease or disorder capable of being modulated by NFκB pathway inhibition.

Other aspects of the disclosure include a compound as disclosed herein for use in the preparation of a medicament for treating or preventing a disease or disorder capable of being modulated by NFκB pathway inhibition in a subject, and the use of a compound as disclosed herein in a method of treating or preventing a disease or disorder capable of being modulated by NFκB pathway inhibition in a subject

DETAILED DESCRIPTION

Figure 1:
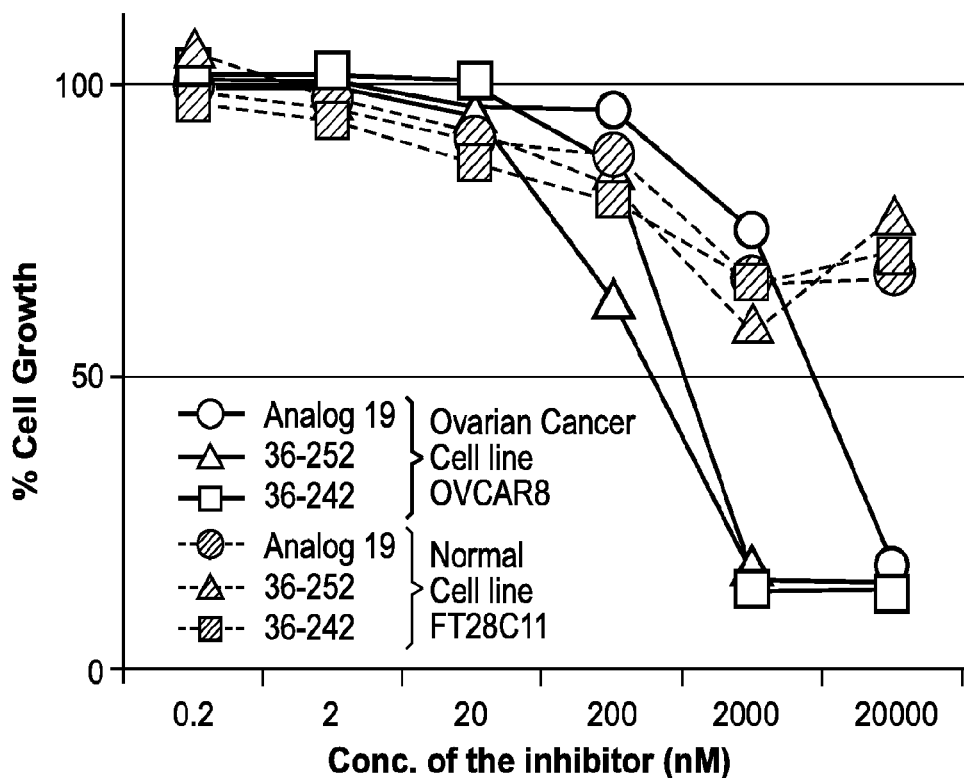
FIG. 1 shows the effect of Compounds 19, 36-252, and 36-242 on cell growth in normal cells (FT28) and ovarian cancer cells (OVCAR5).
Figure 2:
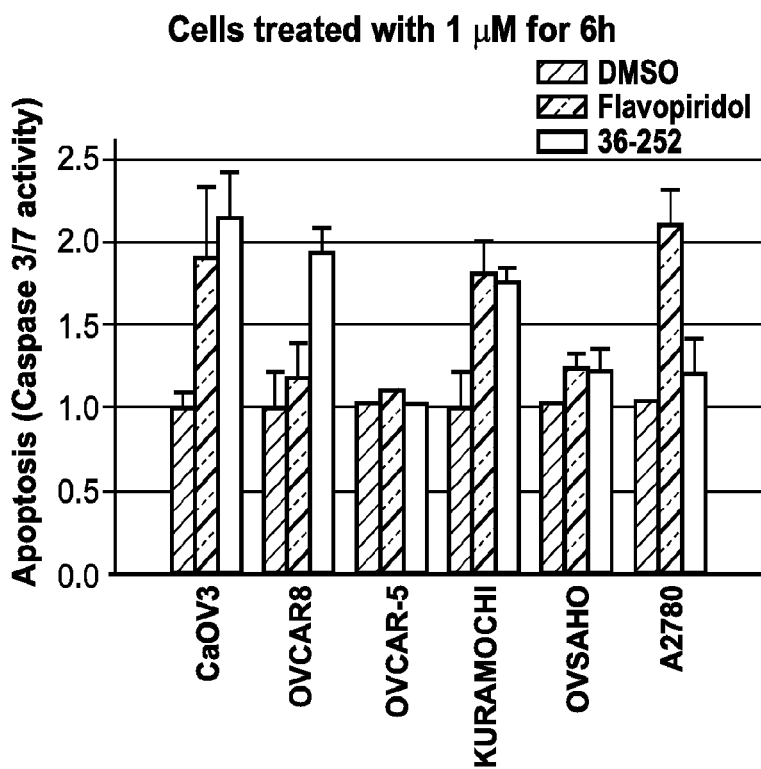
FIG. 2 shows the effect of Control (DMSO), flavopirodol, and compound 36-252 on apoptosis in five HGSC cell lines as measured by a caspase assay.

Provided herein are compounds that inhibit the NFκB pathway, and can treat or prevent a disease or disorder associated with NFκB in a subject. These compounds are useful in the treatment of a variety of diseases and disorders, including but not limited to cancer, autoimmune diseases, inflammatory diseases, diabetes, cardiovascular diseases, or neurological diseases.

Compounds of the Disclosure

The disclosure provides compounds of Formula I:

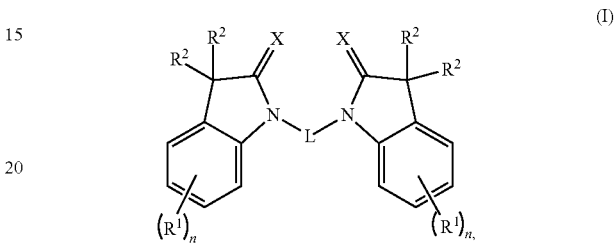

(I)

wherein X is O, S, or $NR^4$;

L is $C_{1-18}$alkylene or $C_{2-18}$alkenylene optionally interrupted with one or more of (i) non-adjacent heteroatom(s) selected from O, S, and $NR^4$, (ii) $C(O)NR^4$, (iii) $C_{6-10}$ aryl, (iv) 5-10 membered heteroaryl having 1-4 heteroatoms selected from N, O, and S, (v) 3-12 membered cycloalkyl ring, and (vi) 3-7 membered heterocycloalkyl ring having 1-3 ring heteroatoms selected from O, S, and N, and said aryl, heteroaryl, cycloalkyl, and heterocycloalkyl are optionally substituted with one or more $R^4$;

each $R^1$ is independently selected from the group consisting of $C_{1-6}$ alkyl, halo, CN, $N(R^4)_2$, $OR^4$, $NO_2$, $CO_2R^4$, $(C=O)R^4$, $CON(R^4)_2$, $NR^4(C=O)R^5$, $C_{6-10}$ aryl, and 5-10 membered heteroaryl having 1-4 heteroatoms selected from N, O, and S, and said alkyl can be optionally substituted with 1 to 3 $R^3$;

each $R^2$ is independently selected from the group consisting of $C_{1-6}$ alkyl, $C_{2-6}$ alkenyl, $C_{2-6}$ alkynyl, halo, $OR^4$, $COR^4$, $CO_2R^4$, $CON(R^4)_2$, $N(R^4)_2$, and $SR^4$, or a pair of two $R^2$ together with the carbon atom to which they are attached form a saturated or unsaturated 4-8 membered cycloalkyl or heterocycloalkyl ring, wherein the heterocycloalkyl ring has 1 or 2 ring heteroatoms selected from O, S, and N, and wherein said alkyl, alkenyl, alkynyl, cycloalkyl ring, and heterocycloalkyl ring are optionally substituted with 1 to 3 $R^3$, with the proviso that at least one $R^2$ or one pair of two $R^2$ together forming a ring comprise an α,β-unsaturated moiety;

each $R^3$ is independently selected from the group consisting of $C_{1-6}$ alkyl, $C_{2-6}$ alkenyl, $C_{2-6}$ alkynyl, halo, CN, $N(R^4)_2$, $OR^4$, $NO_2$, oxo, =S, =$NR^4$, $CO_2R^4$, $(C=O)R^4$, $CON(R^4)_2$, $C_{6-10}$ aryl, and 5-10 membered heteroaryl having 1-4 ring heteroatoms selected from N, O, and S, and wherein said alkyl, alkenyl, and alkynyl are optionally substituted with 1 to 3 $R^4$;

each $R^4$ is independently selected from the group consisting of H, $C_{1-6}$ alkyl, $C_{2-6}$ alkenyl, and $C_{2-6}$ alkynyl, wherein said alkyl, alkenyl, and alkynyl are optionally substituted with one or more substituents selected from the group consisting of halo, CN, $NH_2$, OH, and $C_{1-6}$ alkoxy;

and n is 0-4.

In various embodiments, at least one pair of two $R^2$ together with the carbon atom to which they are attached form a saturated or unsaturated 3-8 membered cycloalkyl or heterocycloalkyl ring. In another embodiment, each pair of $R^2$ together with the carbon atom to which they are attached form a saturated or unsaturated 3-8 membered cycloalkyl or heterocycloalkyl ring. In some cases, at least one pair of two $R^2$ together with the carbon atom to which they are attached form a saturated or unsaturated 5 membered cycloalkyl or heterocycloalkyl ring, wherein the heterocycloalkyl ring has 1 or 2 ring heteroatoms selected from O, S, and N, and wherein said cycloalkyl and heterocycloalkyl ring are optionally substituted with 1 to 3 $R^3$.

In various embodiments, at least one $R^2$ or one pair of two $R^2$ together forming a ring comprise an α,β-unsaturated moiety. In one embodiment, one $R^2$ comprises an α,β-unsaturated moiety. In another embodiment, at least one pair of two $R^2$ together forming a ring comprises an a,I3-unsaturated moiety. In one embodiment, two pairs of two $R^2$ together forming a ring comprise α,β-unsaturated moieties.

In various embodiments, at least one pair of two $R^2$ together with the carbon atom to which they are attached form a ring having the structure:

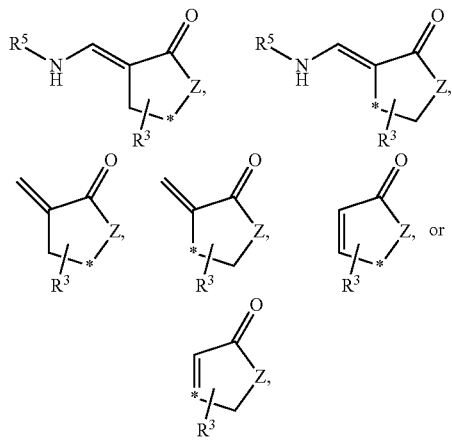

wherein * is the carbon atom to which each $R^2$ is attached, Z is O or $NR^4$, and $R^5$ is $C_{1-6}$alkyl, $C_{2-6}$alkenyl, $C_{6-10}$ aryl, or 3-7 membered heterocycloalkyl ring having 1-3 ring heteroatoms selected from O, S, and N. In some embodiments, one pair of two $R^2$ together with the carbon atom to which they are attached form a ring having the structure:

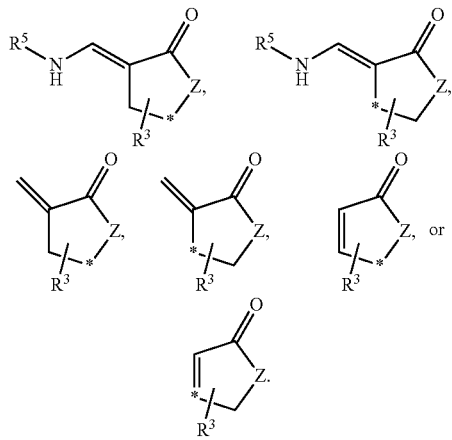

In some embodiments, two pairs of two $R^2$ together with the carbon atom to which they are attached form a ring having the structure:

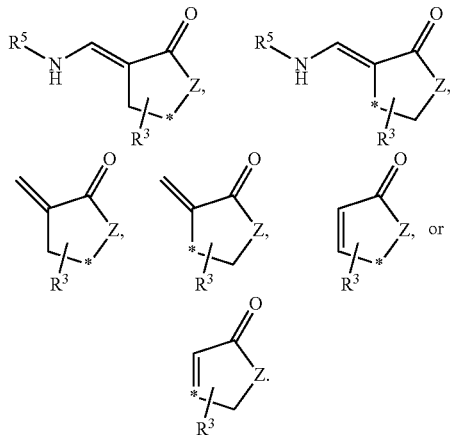

In various embodiments, at least one pair of two $R^2$ together with the carbon atom to which they are attached form a ring having the structure:

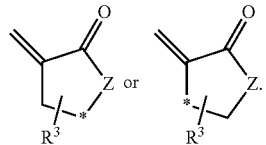

In some embodiments, Z is O or NH. In one embodiment, Z is NH. In another embodiment, Z is O.

In some embodiments, at least one $R^2$ has a structure:

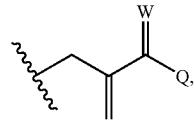

wherein W is O, S, or $NR^4$; and Q is selected from the group consisting of $C_{1-6}$ alkyl, $C_{2-6}$ alkenyl, $C_{2-6}$ alkynyl, $N(R^4)_2$, and $OR^4$. In some embodiments, W is O and Q is $OR^4$. In some embodiments, $R^4$ is H or $C_{1-6}$ alkyl. In one embodiment, $R^4$ is methyl.

The "L" comprises $C_{1-18}$alkylene or $C_{2-18}$alkenylene optionally interrupted with one or more of (i) non-adjacent heteroatom(s) selected from O, S, and $NR^4$, (ii) $C(O)NR^4$, (iii) $C_{6-10}$ aryl, (iv) 5-10 membered heteroaryl having 1-4 heteroatoms selected from N, O, and S, (v) 3-12 membered cycloalkyl ring, and (vi) 3-7 membered heterocycloalkyl ring having 1-3 ring heteroatoms selected from O, S, and N, and said aryl, heteroaryl, cycloalkyl, and heterocycloalkyl are optionally substituted with one or more $R^4$. In some cases, L is interupted with 1-3 of any combination of groups (i)-(vi). In some cases, L is interrupted with 1 group of (i)-(vi). In some embodiments, L is uninterrupted $C_{1-18}$alkylene. In another embodiment, L is uninterrupted $C_{1-12}$alkylene. In various embodiments, L is $C_1$alkylene, $C_2$alkylene, $C_3$alkylene, $C_4$alkylene, $C_5$alkylene, $C_6$alkylene, $C_7$alkylene, $C_8$alkylene, $C_9$alkylene, $C_{10}$alkylene, $C_{11}$alkylene, or $C_{12}$alkylene. In one embodiment, L is $C_7$alkylene. In another embodiment, L is $C_{12}$alkylene.

In some embodiments, L is

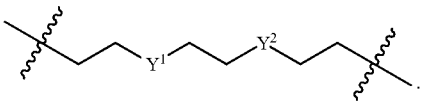

In another embodiment, at least one of $Y^1$ and $Y^2$ is O. In another embodiment, each of $Y^1$ and $Y^2$ are O. In another embodiment, at least one of $Y^1$ and $Y^2$ is $NR^4$. In another embodiment, each of $Y^1$ and $Y^2$ are $NR^4$. In some embodiments, $R^4$ is H or $C_{1-6}$ alkyl. In one embodiment, $R^4$ is methyl.

In some embodiments, L is $C_{2-18}$alkenylene. In various embodiments, L is $C_2$alkenylene, $C_3$alkenylene, $C_4$alkenylene, $C_5$alkenylene, $C_6$alkenylene, $C_7$alkenylene, $C_8$alkenylene, $C_9$alkenylene, $C_{10}$alkenylene, $C_{11}$alkenylene, or $C_{12}$alkenylene. In some embodiments, L comprises one carbon-carbon double bond. In some embodiments, L comprises two carbon-carbon double bonds. In one embodiment, L is

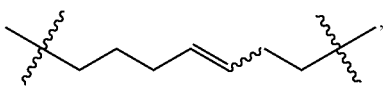

and ∿ indicates that the double bond is cis or trans. In another embodiment, L is or

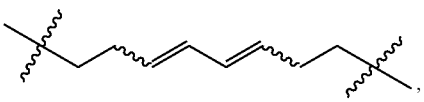 [SMILES: *CCC=CC=CCC*]

and ∿ indicates that the double bond is cis or trans. In some embodiments, at least one double bond is cis. In some embodiments, at least one double bond is trans. In some embodiments, two double bonds are cis. In some embodiments, two double bonds are trans. In some embodiments, one double bond is cis, and the other double bond is trans.

In some embodiments, L comprises a 3-12 membered cycloalkyl ring optionally substituted with one or more $R^4$. In some embodiments, L comprises a 5 or 6 membered cycloalkyl ring optionally substituted with one or more $R^4$. In one embodiment, L is

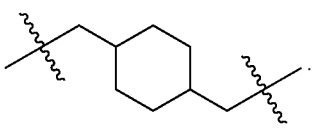 [SMILES: *CC1CCC(C*)CC1]

In another embodiment, L is

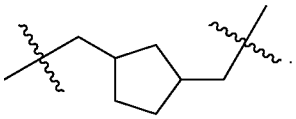 [SMILES: *CC1CCC(C*)C1]

In some embodiments, L is $C_{1-18}$alkylene or $C_{2-18}$alkenylene interrupted by at least one phenyl. In some embodiments, L is interrupted by $C_{1-18}$alkylene or $C_{2-18}$alkenylene interrupted by one phenyl. In some embodiments, L is interrupted by $C_{1-18}$alkylene or $C_{2-18}$alkenylene interrupted by two phenyls. In various embodiments, L is

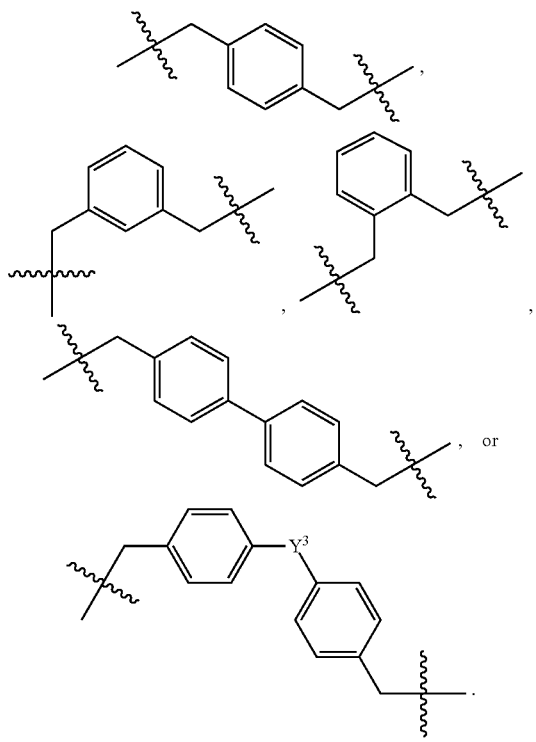

, or

In one embodiment, L is

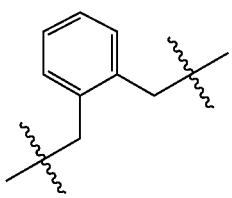

In some embodiments, $Y^3$ is O. In another embodiment, $Y^3$ is $NR^4$. In a further embodiment, $R^4$ is methyl.

In some embodiments, L is

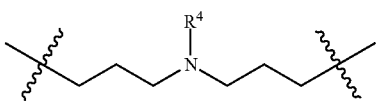

In another embodiment, $R^4$ is $C_{2-6}$ alkynyl. In another embodiment, $R^4$ is 4-butynyl.

Further provided are compounds as recited in Table A, or a pharmaceutically acceptable salt thereof. Also provided are use of compounds recited in Table A, or a pharmaceutically acceptable salt thereof.

Specific compounds contemplated include those listed in Table 1, or a pharmaceutically acceptable salt thereof:

TABLE 1

| Compound # | Structure |
|---|---|
| 19 | 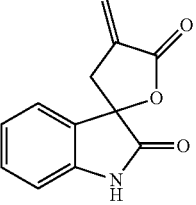 [SMILES: C=C1CC2(OC1=O)C(=O)Nc1ccccc12] |
| 20 | 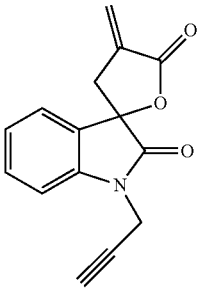 [SMILES: C#CCN1C(=O)C2(CC(=C)C(=O)O2)c2ccccc21] |
| 21 | 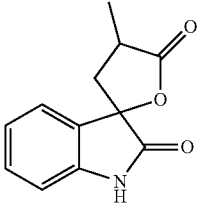 [SMILES: CC1CC2(OC1=O)C(=O)Nc1ccccc12] |
| 22 | 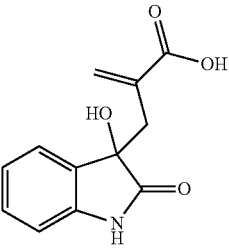 [SMILES: C=C(CC1(O)C(=O)Nc2ccccc21)C(=O)O] |
| 40-059 | 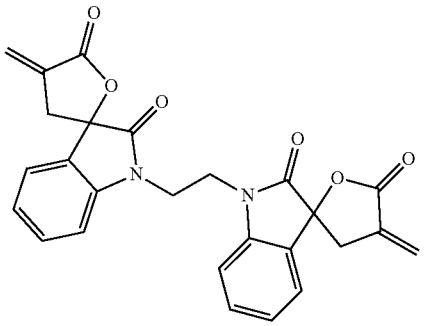 |

TABLE 1-continued

| Compound # | Structure |
|---|---|
| 36-286 | 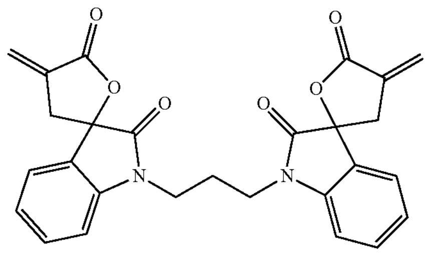 |
| 40-039 | 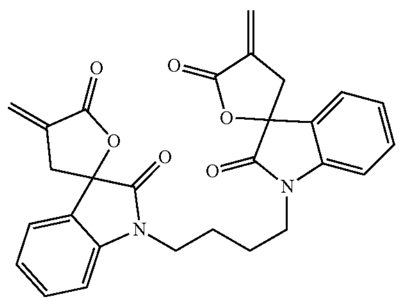 [SMILES: C=C1CC2(OC1=O)C(=O)N(CCCCN1C(=O)C3(CC(=C)C(=O)O3)c3ccccc31)c1ccccc12] |
| 36-202 | 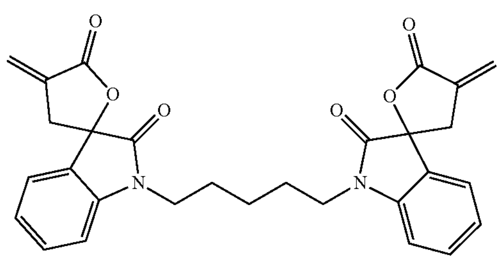 |
| 36-239 | 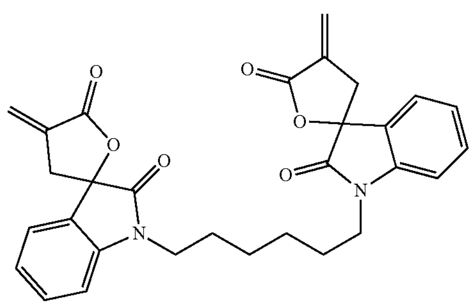 [SMILES: C=C1CC2(OC1=O)C(=O)N(CCCCCCN1C(=O)C3(CC(=C)C(=O)O3)c3ccccc31)c1ccccc12] |
| 36-252 | 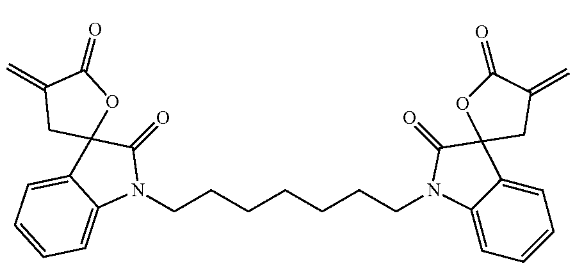 |

TABLE 1-continued
| Compound # | Structure |
|---|---|
| 36-254 | 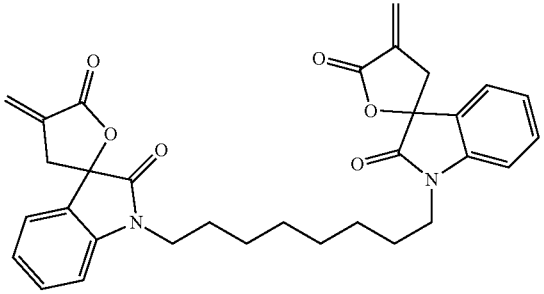 [SMILES: C=C1CC2(OC1=O)C(=O)N(CCCCCCCCN1C(=O)C3(CC(=C)C(=O)O3)c3ccccc31)c1ccccc12] |
| 36-204 | 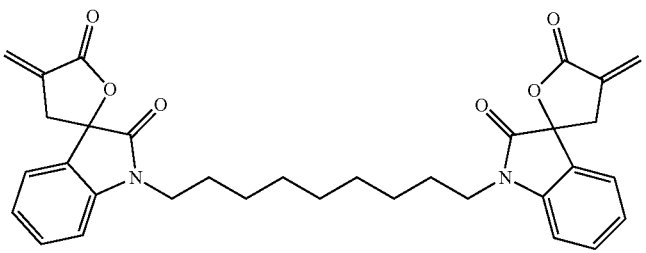 |
| 36-256 | 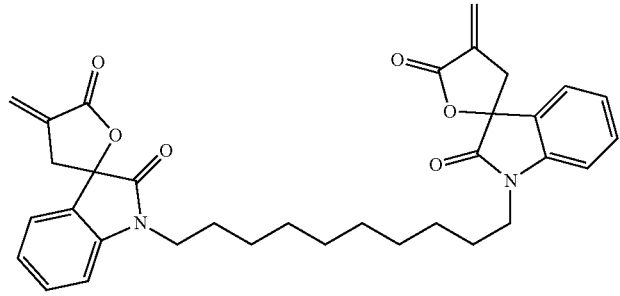 [SMILES: C=C1CC2(OC1=O)C(=O)N(CCCCCCCCCCN1C(=O)C3(CC(=C)C(=O)O3)c3ccccc31)c1ccccc12] |
| 36-258 | 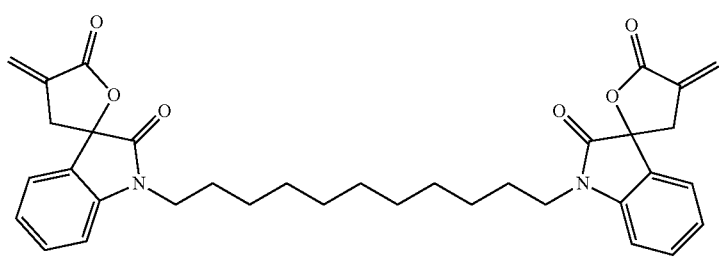 |
| 36-242 | 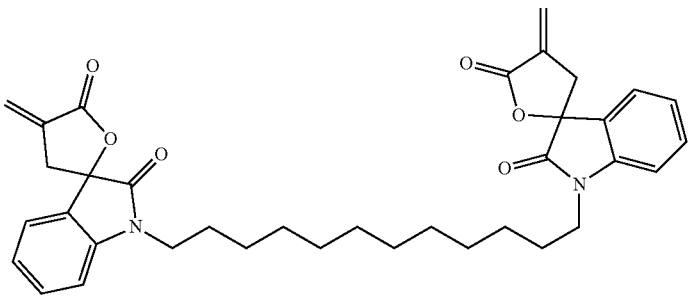 [SMILES: C=C1CC2(OC1=O)C(=O)N(CCCCCCCCCCCCN1C(=O)C3(CC(=C)C(=O)O3)c3ccccc31)c1ccccc12] |

TABLE 1-continued

| Compound # | Structure |
|---|---|
| 36-280 | 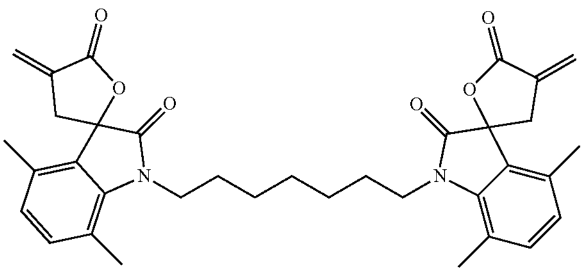 |
| 36-297 | 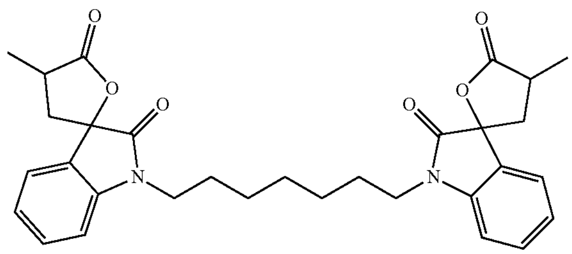 |
| 40-014 | 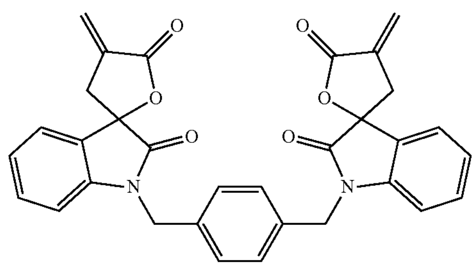 [SMILES: C=C1CC2(OC1=O)C(=O)N(Cc1ccc(CN3C(=O)C4(CC(=C)C(=O)O4)c4ccccc43)cc1)c1ccccc12] |
| 36-252P | 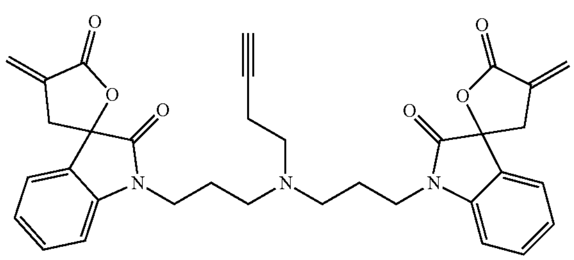 |
| 36-252N | 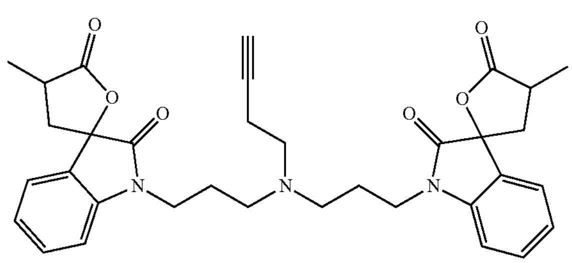 |
| P1 | 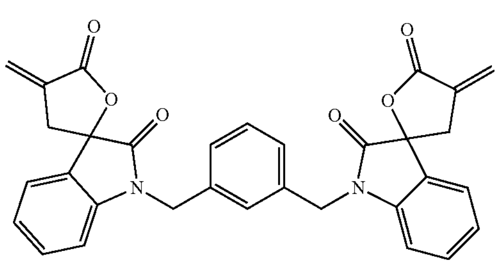 |

TABLE 1-continued

| Compound # | Structure |
|---|---|
| P2 | (structure image) |
| P3 | (structure image) |
| P4 | (structure image) |
| P5 | (structure image) |
| P6 | (structure image) |
| P7 | (structure image) |

TABLE 1-continued

| Compound # | Structure |
| --- | --- |
| P8 | 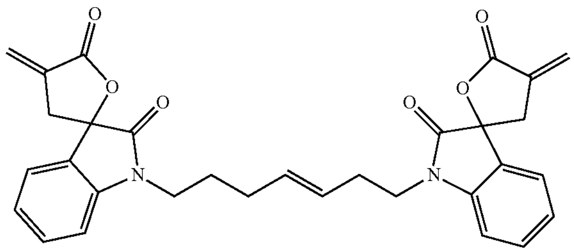 |
| P9 | 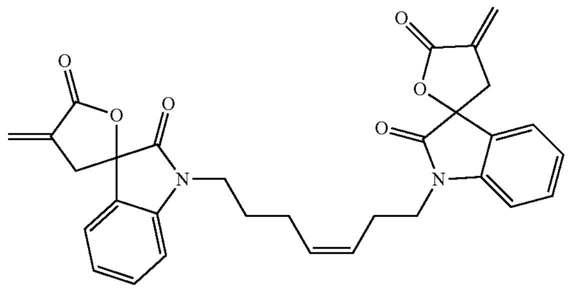 [SMILES: C=C1CC2(OC1=O)C(=O)N(CC/C=C\CCCN1C(=O)C3(CC(=C)C(=O)O3)c3ccccc31)c1ccccc12] |
| P10 | 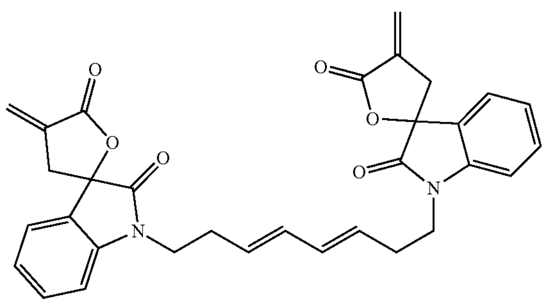 [SMILES: C=C1CC2(OC1=O)C(=O)N(CC/C=C/C=C/CCN1C(=O)C3(CC(=C)C(=O)O3)c3ccccc31)c1ccccc12] |
| P11 | 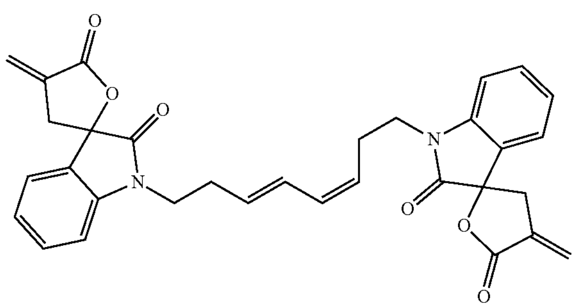 |
| P12 | 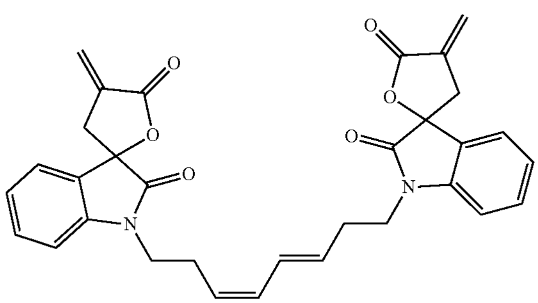 [SMILES: C=C1CC2(OC1=O)C(=O)N(CC/C=C\C=C\CCN1C(=O)C3(CC(=C)C(=O)O3)c3ccccc31)c1ccccc12] |

TABLE 1-continued
| Compound # | Structure |
|---|---|
| P13 | 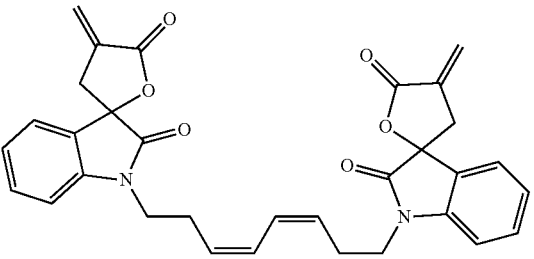 [SMILES: C=C1CC2(OC1=O)C(=O)N(CC/C=C\C=C/CCN1C(=O)C3(CC(=C)C(=O)O3)c3ccccc31)c1ccccc12] |
| P14 | 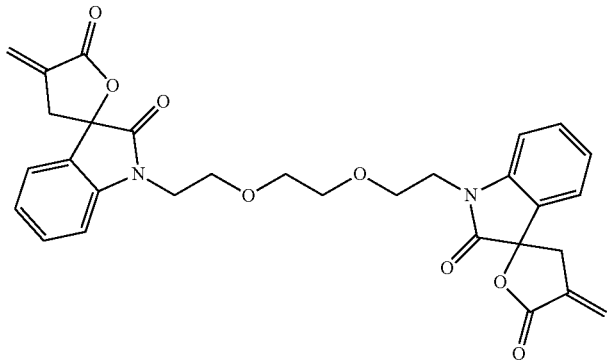 |
| P15 | 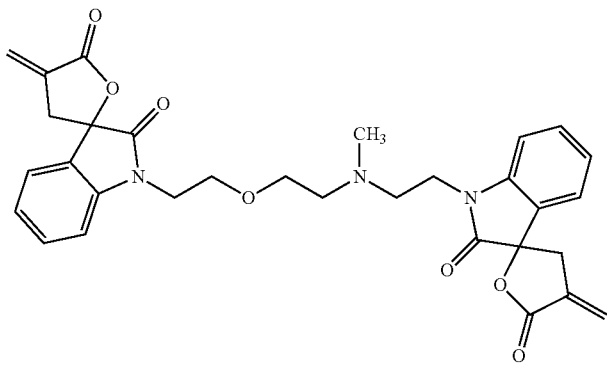 |
| P16 | 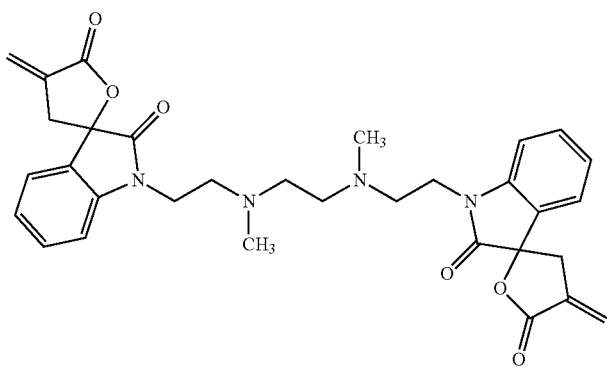 |

TABLE 1-continued

| Compound # | Structure |
| --- | --- |
| 25-4 | 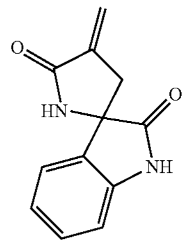 [SMILES: C=C1CC2(NC1=O)C(=O)Nc1ccccc12] |
| P17 | 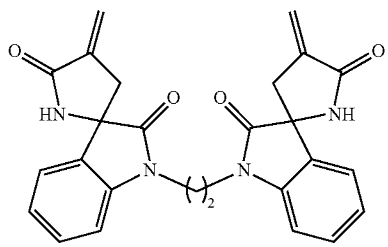 |
| P18 | 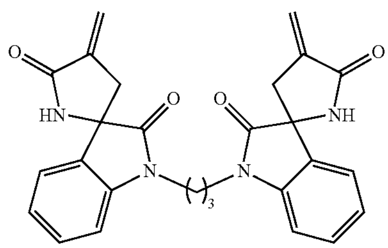 |
| 40-038 | 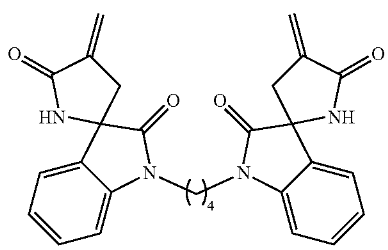 |
| P19 | 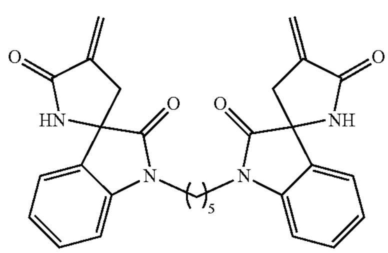 |
| P20 | 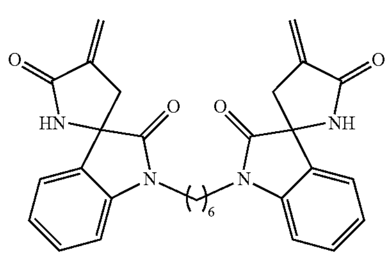 |

TABLE 1-continued

| Compound # | Structure |
|---|---|
| P21 | (bis-spiroindolinone-pyrrolidinone linked by -(CH2)7-) |
| P22 | (bis-spiroindolinone-pyrrolidinone linked by -(CH2)8-) |
| P23 | (bis-spiroindolinone-pyrrolidinone linked by -(CH2)9-) |
| P24 | (bis-spiroindolinone-pyrrolidinone linked by -(CH2)10-) |
| P25 | (bis-spiroindolinone-pyrrolidinone linked by -(CH2)11-) |
| P26 | (bis-spiroindolinone-pyrrolidinone linked by -(CH2)12-) |

TABLE 1-continued

| Compound # | Structure |
|---|---|
| P27 | 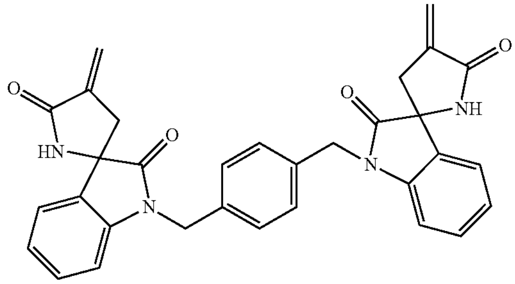 [SMILES: C=C1CC2(NC1=O)C(=O)N(Cc1ccc(CN3C(=O)C4(CC(=C)C(=O)N4)c4ccccc43)cc1)c1ccccc12] |
| P28 | 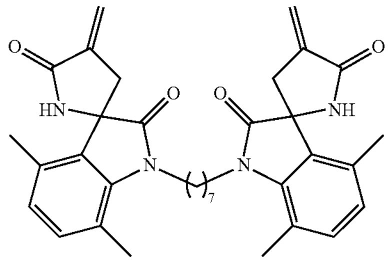 |
| P29 | 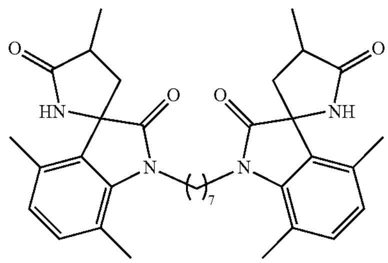 |

The compounds disclosed herein can be in the form of a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66, 1-19, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (e.g., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

The term "alkylene" used herein refers to an alkyl group having a substituent. For example, the term "alkylenehalo" refers to an alkyl group substituted with a halo group. For example, an alkylene group can be —CH$_2$CH$_2$— or —CH$_2$—. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups. Unless otherwise indicated, an alkylene group can be an unsubstituted alkylene group or a substituted alkylene group.

The term "alkenyl" used herein refers to an unsaturated aliphatic group analogous in length and possible substitution to an alkyl group described above, but that contains at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. For example, a straight chain or branched alkenyl group can have six or fewer carbon atoms in its backbone (e.g., $C_2$-$C_6$ for straight chain, $C_3$-$C_6$ for branched chain). The term "$C_2$-$C_6$" includes chains having a number of carbon atoms encompassing the entire range (e.g., 2 to 6 carbon atoms), as well as all subgroups (e.g., 2-6, 2-5, 2-4, 3-6, 2, 3, 4, 5, and 6 carbon atoms). The term "$C_3$-$C_6$" includes chains having a number of carbon atoms encompassing the entire range (e.g., 3 to 6 carbon atoms), as well as all subgroups (e.g., 3-6, 3-5, 3-4, 3, 4, 5, and 6 carbon atoms). Unless otherwise indicated, an alkenyl group can be an unsubstituted alkenyl group or a substituted alkenyl group.

The term "alkenylene" used herein refers to an alkenyl group having a substituent. For example, the term "alkenylenehalo" refers to an alkyl group substituted with a halo group. For example, an alkylene group can be —CH=CH—. The term $C_n$ means the alkenylene group has "n" carbon atoms. For example, $C_{2-6}$alkenylene refers to an alkenylene group having a number of carbon atoms encompassing the entire range, as well as all subgroups, as previously described for "alkenyl" groups. Unless otherwise indicated, an alkenylene group can be an unsubstituted alkenylene group or a substituted alkenylene group.

As used herein, an alkylene or alkenylene which is "optionally interrupted" is understood to be an alkylene or alkenylene group in which at one or more (e.g., 1-5, 1-4, 1-3, 1-2, 1, 2, 3, 4, or 5) positions on the alkylene or alkenylene chain is inserted a group selected from heteroatoms, aryl rings, heteroaryl rings, cycloalkyl rings, or heterocycloalkyl rings. The interruptions can be consecutive for various combinations of these interrupting groups (e.g., a heteroatom next to a heteroaryl moiety), except that two heteroatoms cannot be adjacent or consecutive to each other. An alkylene or alkenylene in which no such inserted group is included is referred to as "uninterrupted".

As used herein an alkylene or alkenylene which is optionally interrupted with "one or more" groups is understood to be optionally interrupted with from 1 to n-1 groups, wherein n is the number of carbon atoms in the alkylene or alkenylene chain. For example, a $C_6$-alkylene which is optionally interrupted with one or more groups can be interrupted with one, two, three, four, or five groups.

The term "alkynyl" used herein refers to an unsaturated aliphatic group analogous in length and possible substitution to an alkyl group described above, but that contains at least one triple bond. For example, the term "alkynyl" includes straight chain alkynyl groups (e.g., ethynyl, propynyl, butynyl, pentynyl, hexynyl, heptynyl, octynyl, nonynyl, decynyl), and branched alkynyl groups. For example, a straight chain or branched alkynyl group can have six or fewer carbon atoms in its backbone (e.g., $C_2$-$C_6$ for straight chain, $C_4$-$C_6$ for branched chain). The term "$C_2$-$C_6$" includes chains having a number of carbon atoms encompassing the entire range (e.g., 2 to 6 carbon atoms), as well as all subgroups (e.g., 2-6, 2-5, 2-4, 3-6, 2, 3, 4, 5, and 6 carbon atoms). The term "$C_4$-$C_6$" includes chains having a number of carbon atoms encompassing the entire range (e.g., 4 to 6 carbon atoms), as well as all subgroups (e.g., 4-6, 4-5, 4, 5, and 6 carbon atoms). Unless otherwise indicated, an alkynyl group can be an unsubstituted alkynyl group or a substituted alkynyl group.

As used herein, the term "cycloalkyl" refers to an aliphatic cyclic hydrocarbon group containing three to twelve carbon atoms (e.g., 3, 4, 5, 6, 7, 8, 9, 10, 11, or 12 carbon atoms). The term $C_n$ means the cycloalkyl group has "n" carbon atoms. For example, $C_5$cycloalkyl refers to a cycloalkyl group that has 5 carbon atoms in the ring. $C_6$-$C_{10}$ cycloalkyl refers to cycloalkyl groups having a number of carbon atoms encompassing the entire range (e.g., 6 to 10 carbon atoms), as well as all subgroups (e.g., 6-7, 6-8, 7-8, 6-9, 6, 7, 8, 9, and 10 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group. When a cycloalkyl group is fused to another cycloalkyl group, then each of the cycloalkyl groups can contain three to twelve carbon atoms unless specified otherwise. Unless otherwise indicated, a cycloalkyl group can be unsubstituted or substituted.

As used herein, the term "heterocycloalkyl" is defined similarly as cycloalkyl, except the ring contains one to three heteroatoms independently selected from oxygen, nitrogen, and sulfur. In particular, the term "heterocycloalkyl" refers to a ring containing a total of three to ten atoms (e.g., three to seven, or five to ten), of which 1, 2, 3 or three of those atoms are heteroatoms independently selected from the group consisting of oxygen, nitrogen, and sulfur, and the remaining atoms in the ring are carbon atoms. Nonlimiting examples of heterocycloalkyl groups include piperdine, pyrazolidine, tetrahydrofuran, tetrahydropyran, dihydrofuran, morpholine, and the like.

Cycloalkyl and heterocycloalkyl groups can be saturated or partially unsaturated ring systems optionally substituted with, for example, one to three groups, independently selected from $C_{1-6}$ alkyl, $C_{2-6}$ alkenyl, $C_{2-6}$ alkynyl, halo, CN, N(R$^4$)$_2$, OR$^4$, NO$_2$, oxo, =S, =NR$^4$, CO$_2$R$^4$, (C=O)R$^4$, CON(R$^4$)$_2$, $C_{6-10}$ aryl, and 5-10 membered heteroaryl. Heterocycloalkyl groups optionally can be further N-substituted with alkyl, alkylene-OH, alkylenearyl, and alkyleneheteroaryl. The heterocycloalkyl groups described herein can be isolated or fused to another heterocycloalkyl group, a cycloalkyl group, an aryl group, and/or a heteroaryl group. When a heterocycloalkyl group is fused to another heterocycloalkyl group, then each of the heterocycloalkyl groups can contain three to ten total ring atoms, and one to three heteroatoms. Unless otherwise indicated, a heterocycloalkyl group can be unsubstituted or substituted.

As used herein, the term "aryl" refers to a monocyclic aromatic group, such as phenyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Other substituents are also contemplated, including $C_{0-3}$alkylene-halo, $C_{0-3}$alkylene-CN, $C_{0-3}$alkylene-$NH_2$, $C_{0-3}$alkylene-OH, and $C_{0-3}$alkylene-O—$C_{1-3}$alkyl. Aryl groups can be isolated (e.g., phenyl) or fused to another aryl group (e.g., naphthyl, anthracenyl), a cycloalkyl group (e.g. tetraydronaphthyl), a heterocycloalkyl group, and/or a heteroaryl group. Exemplary aryl groups include, but are not limited to, phenyl, chlorophenyl, methylphenyl, methoxyphenyl, trifluoromethylphenyl, nitrophenyl, 2,4-methoxychlorophenyl, and the like. Throughout, the abbreviation "Ph" refers to phenyl and "Bn" refers to benzyl (i.e., $CH_2$phenyl).

As used herein, the term "heteroaryl" refers to a monocyclic aromatic ring having 5 to 10 total ring atoms, and containing one to four heteroatoms selected from nitrogen, oxygen, and sulfur atom in the aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Other substituents are also contemplated, including $C_{0-3}$alkylene-halo, $C_{0-3}$alkylene-CN, $C_{0-3}$alkylene-N $H_2$, $C_{0-3}$alkylene-OH, and $C_{0-3}$alkylene-O—$C_{1-3}$alkyl. In some cases, the heteroaryl group is substituted with one or more of alkyl and alkoxy groups. Examples of heteroaryl groups include, but are not limited to, thienyl, furyl, pyridyl, pyrrolyl, oxazolyl, triazinyl, triazolyl, isothiazolyl, isoxazolyl, imidazolyl, pyrazinyl, pyrimidinyl, thiazolyl, and thiadiazolyl.

As used herein, the term "alkoxy" or "alkoxyl" as used herein refers to a "—O-alkyl" group. The alkoxy or alkoxyl group can be unsubstituted or substituted.

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, aryl, heteroaryl, hydroxyl, oxy, alkoxy, heteroalkoxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms.

As used herein, the phrase "optionally substituted" means unsubstituted (e.g., substituted with a H) or substituted. As used herein, the term "substituted" means that a hydrogen atom is removed and replaced by a substituent. It is understood that substitution at a given atom is limited by valency. The use of a substituent (radical) prefix name such as alkyl without the modifier "optionally substituted" or "substituted" is understood to mean that the particular substituent is unsubstituted.

As used herein, the term "α,β-unsaturated moiety" refers to a functional group bearing an unsaturated bond between alpha and beta carbons (e.g., an alkene) adjacent to a carbon having a double bond to a heteroatom, for example, oxygen (e.g., a carbonyl), sulfur (e.g., a thiocarbonyl), or nitrogen (e.g., an imine). An α,β-unsaturated moiety can be an electrophile capable of undergoing an addition reaction, e.g., a Michael addition. Electrophilic α,β-unsaturated moieties which can undergo an addition reaction are also called Michael acceptors. An α,β-unsaturated moiety can be part of a chain or a ring structure in a molecule. An α,β-unsaturated moiety can have the structure

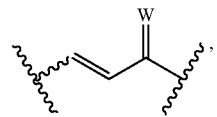

wherein W is a heteroatom (e.g., O, S, or N), and ∼∼ indicates that the double bond can be cis or trans. Nonlimiting examples of α,β-unsaturated moieties include α,β-unsaturated carbonyl compounds (e.g., enones, enals, α,β-unsaturated esters, and α,β-unsaturated amides), α,β-unsaturated thioesters, α,β-unsaturated thiones, α,β-unsaturated thioates, α,β-unsaturated imines, and α,β-unsaturated amidines.

As used herein, the term "therapeutically effective amount" means an amount of a compound or combination of therapeutically active compounds (e.g., a NFκB modulator or combination of NFκB modulators) that ameliorates, attenuates or eliminates one or more symptoms of a particular disease or condition (e.g., cancer), or prevents or delays the onset of one of more symptoms of a particular disease or condition.

As used herein, the terms "patient" and "subject" may be used interchangeably and mean animals, such as dogs, cats, cows, horses, and sheep (e.g., non-human animals) and humans. Particular patients or subjects are mammals (e.g., humans). The terms patient and subject include males and females.

As used herein, the term "pharmaceutically acceptable" means that the referenced substance, such as a compound of the present disclosure, or a formulation containing the compound, or a particular excipient, are safe and suitable for administration to a patient or subject. The term "pharmaceutically acceptable excipient" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

Synthesis of Compounds of the Disclosure

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5$^{th}$ edition, John Wiley & Sons: New York, 2001 ; and Greene, T. W., Wuts, P. G. M., Protective Groups in Organic Synthesis, 3$^{rd}$ edition, John Wiley & Sons: New York, 1999, are useful and recognized reference textbooks of organic synthesis known to those in the art. For example, the compounds disclosed herein can be synthesized by solid phase synthesis techniques including those described in Merrifield, J. Am. Chem. Soc. 1963; 85:2149; Davis et al., Biochem. Intl. 1985; 10:394-414; Larsen et al., J. Am. Chem. Soc. 1993; 115:6247; Smith et al., J. Peptide Protein Res. 1994; 44: 183; O'Donnell et al., J. Am. Chem. Soc. 1996; 118:6070; Stewart and Young, Solid Phase Peptide Synthesis- Freeman (1969); Finn et al., The Proteins, 3rd ed., vol. 2, pp. 105-253 (1976); and Erickson et al., The Proteins, 3rd ed., vol. 2, pp. 257-527 (1976). The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt, ester or prodrug thereof.

In general, compounds of Formula I can be synthesized according to Scheme 1.

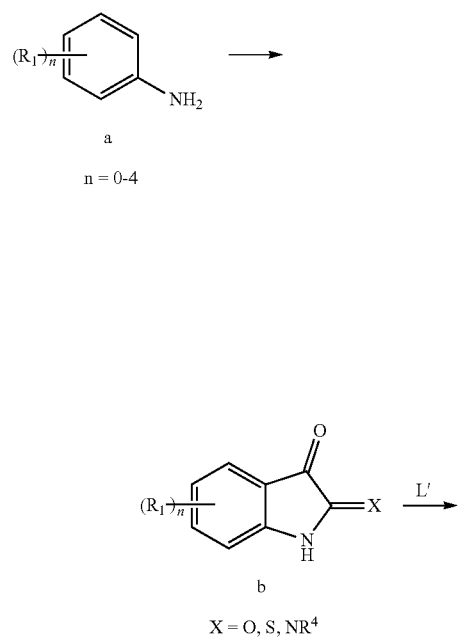

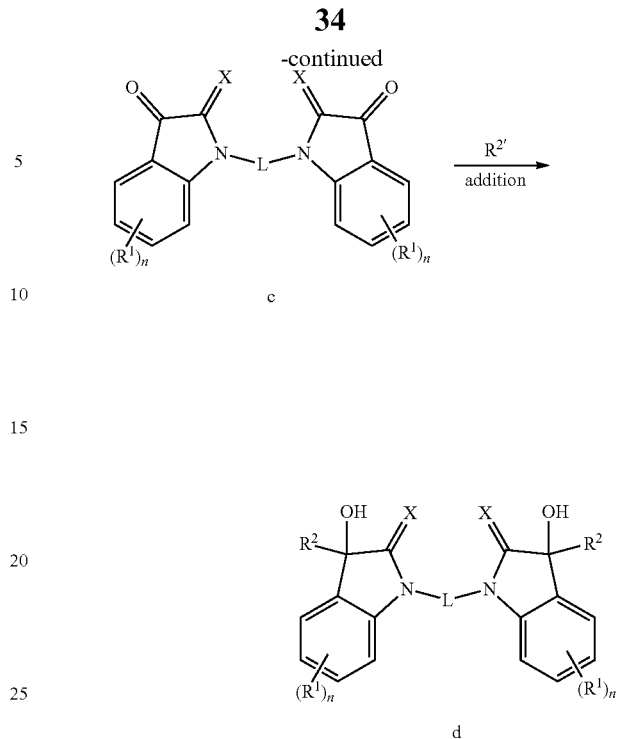

Compounds having structure d can be synthesized using the procedure shown in Scheme 1. Condensation of an optionally substituted aniline a with appropriate reagents, e.g., chloral hydrate, amonium hydroxide, and concentrated sulfuric acid, produces an isatin or isatin derivative compound b. Reaction of b with an appropriate bifunctional compound L' produces dimers having structure c. Subsequent addition of an appropriate reagent R$^{2'}$ gives compounds as described herein, i.e., compounds of Formula I having structure d. Appropriate addition conditions will be known to those skilled in the art, but are contemplated to include, without limitation, transition metal catalyzed additions such as indium catalyzed additions (e.g., a Barbier reaction).

The addition reaction to form d can be catalyzed by appropriate reagents selected based on the precise nature of compounds c and R$^{2'}$. For example, when R$^{2'}$ is an allyl halide compound, the coupling of compounds c and R$^{2'}$ can be an indium-mediated allylation. Occasionally, the coupling reaction may not require a catalyst.

Compounds a, L', and R$^{2'}$ can be purchased commercially or prepared by a variety of methods from commercially-available starting materials. For example, L' can be a dibromoalkyl compound, such as dibromoheptane or dibromododecane. Similarly, R$^{2'}$ can be an allyl halide compound, such as methyl 2-(bromomethyl)acrylate.

Derivatization reactions to transform compounds having structure d into other compounds of Formula I can be selected based on the nature of the substituent R$^{2}$ and the functionality desired. For example, R$^{2}$ can comprise an ester group, which can be hydrolyzed (e.g., by treatment with tosic acid) to a carboxylic acid group, which can be further derivatized by methods known in the art to form a variety of functional groups, including by cyclization as shown in Scheme 2.

Scheme 2

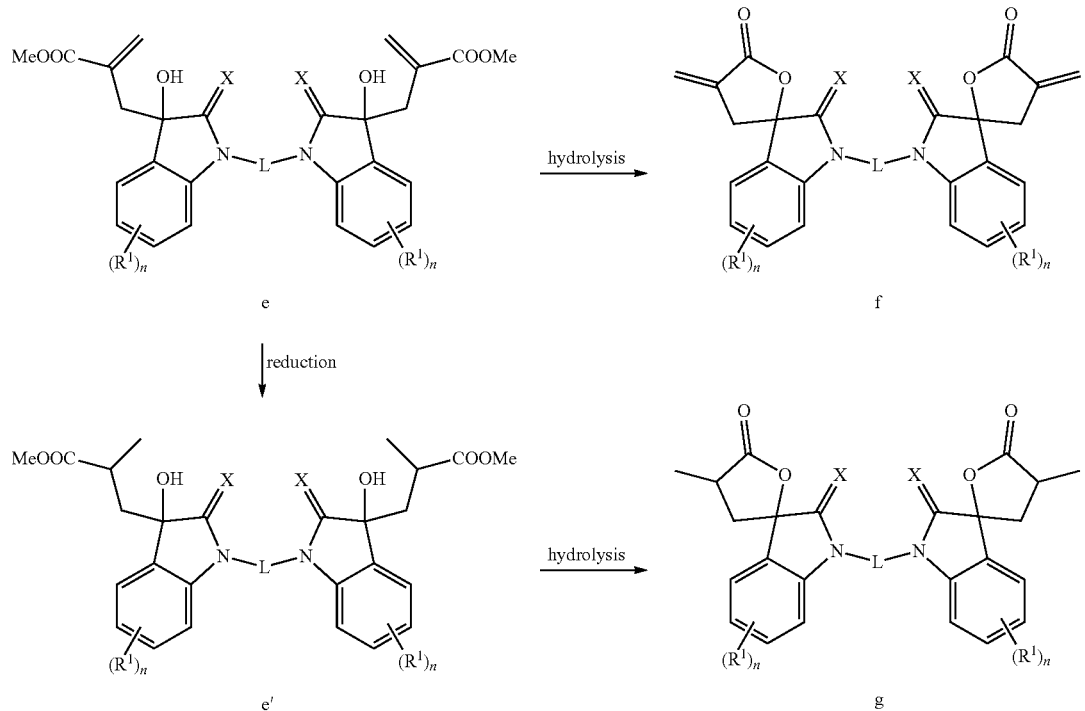

Additional compounds as described herein (i.e., spirocyclic compounds of Formula I) having structure f or g can be synthesized using the procedure shown in Scheme 2. For example, hydrolysis of optionally bis-methacrylate compound e (e.g., by treatment with tosic acid) leads to an intramolecular cyclization, forming a compound having structure f. Reduction of compound e (e.g., via palladium-catalyzed hydrogenation) gives compounds having structure e'. Subsequent hydrolysis forms additional compounds as described herein, i.e., compounds having structure g.

Additional synthetic procedures for preparing the compounds disclosed herein can be found in the Examples section.

Pharmaceutical formulations, dosing, and routes of administration

Further provided are pharmaceutical formulations comprising a compound as described herein (e.g., compounds of Formula I or pharmaceutically acceptable salts of the compounds) and a pharmaceutically acceptable excipient.

The compounds described herein can be administered to a subject in a therapeutically effective amount (e.g., in an amount sufficient to prevent or relieve the symptoms of a disorder associated with aberrant NFκB activity). The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

A particular administration regimen for a particular subject will depend, in part, upon the compound, the amount of compound administered, the route of administration, and the cause and extent of any side effects. The amount of compound administered to a subject (e.g., a mammal, such as a human) in accordance with the disclosure should be sufficient to effect the desired response over a reasonable time frame. Dosage typically depends upon the route, timing, and frequency of administration. Accordingly, the clinician titers the dosage and modifies the route of administration to obtain the optimal therapeutic effect, and conventional range-finding techniques are known to those of ordinary skill in the art.

Purely by way of illustration, the method comprises administering, e.g., from about 0.1 mg/kg up to about 100 mg/kg of compound or more, depending on the factors mentioned above. In other embodiments, the dosage ranges from 1 mg/kg up to about 100 mg/kg; or 5 mg/kg up to about 100 mg/kg; or 10 mg/kg up to about 100 mg/kg. Some conditions require prolonged treatment, which may or may not entail administering lower doses of compound over multiple administrations. If desired, a dose of the compound is administered as two, three, four, five, six or more sub-doses administered separately at appropriate intervals throughout the day, optionally, in unit dosage forms. The treatment period will depend on the particular condition and type of pain, and may last one day to several months.

Suitable methods of administering a physiologically-acceptable composition, such as a pharmaceutical composition comprising the compounds disclosed herein (e.g., compounds of Formula I), are well known in the art. Although more than one route can be used to administer a compound, a particular route can provide a more immediate and more effective reaction than another route. Depending on the circumstances, a pharmaceutical composition comprising the compound is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection by intravenous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the compound is administered regionally via intrathecal administration, intracerebral (intra-parenchymal) administration, intracerebroventricular administration, or intraarterial or intravenous administration feeding the region of interest. Alternatively, the composition is administered locally via implantation of a membrane, sponge, or another appropriate material onto which the desired compound has been absorbed or encapsulated. Where an implantation device is used, the device is, in one aspect, implanted into any suitable tissue or organ, and delivery of the desired compound is, for example, via diffusion, timed-release bolus, or continuous administration.

To facilitate administration, the compound is, in various aspects, formulated into a physiologically-acceptable composition comprising a carrier (e.g., vehicle, adjuvant, or diluent). The particular carrier employed is limited only by chemico-physical considerations, such as solubility and lack of reactivity with the compound, and by the route of administration. Physiologically-acceptable carriers are well known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986)). A pharmaceutical composition comprising the compound is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compositions used in the methods of the invention may be formulated in micelles or liposomes. Such formulations include sterically stabilized micelles or liposomes and sterically stabilized mixed micelles or liposomes. Such formulations can facilitate intracellular delivery, since lipid bilayers of liposomes and micelles are known to fuse with the plasma membrane of cells and deliver entrapped contents into the intracellular compartment.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, 18th Ed. (1990) Mack Publishing Co., Easton, Pa., pages 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

The precise dosage to be employed depends upon several factors including the host, whether in veterinary medicine or human medicine, the nature and severity of the condition, e.g., disease or disorder, being treated, the mode of administration and the particular active substance employed. The compounds may be administered by any conventional route, in particular enterally, and, in one aspect, orally in the form of tablets or capsules. Administered compounds can be in the free form or pharmaceutically acceptable salt form as appropriate, for use as a pharmaceutical, particularly for use in the prophylactic or curative treatment of a disease of interest. These measures will slow the rate of progress of the disease state and assist the body in reversing the process direction in a natural manner.

It will be appreciated that the pharmaceutical compositions and treatment methods of the invention are useful in fields of human medicine and veterinary medicine. Thus the subject to be treated is in one aspect a mammal. In another aspect, the mammal is a human.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of use

The compounds described herein (e.g., the compounds of Formula I or compounds of Table 1) can inhibit an NFκB pathway. In some embodiments, the compounds bind to NFκB, IκB α, IKK-beta, and IKK-alpha leading to their inhibition and degradation, e.g., the compounds trigger or inhibit NFκB -mediated biological activity, such as gene expression. In various embodiments, the compounds are NFκB modulators, e.g., the compounds change, inhibit, or prevent one or more of the NFκB pathway's biological activities.

The compounds disclosed herein are particularly advantageous for the treatment of diseases or disorders caused by aberrant expression or activity of an NFκB pathway. The incidence and/or intensity of diseases or disorders associated with aberrant expression or activity of an NFκB pathway is reduced.

Transduction of the NFκB pathway signals are initiated through external stimuli of a cell. A ligand, such as cytokines or TNFα, binds to its plasma transmembrane cell receptor, activating the receptor. The signal is then transduced from the receptors through the canonical NFκB pathway (involving NFκB1) and/or the alternative NFκB pathway (involving NFκB2). In the canonical pathway, a complex of IκBα kinase (IKK) proteins, IKKα/β/γ, is activated and phosphorylates the protein IκBα, which is associated with p50 and p65, causing dissociation of IκBα. The IκBα interaction with p50 and p65 is inhibitory, and p50/p65 is then activated through dissociation of IκBα. The p50/p65 complex is imported into the nucleus where it acts as a transcription factor, thus activating gene transcription. In the alternative pathway, the signal from the cell receptor is transmitted through the protein NIK, which activates IKKα. This ultimately activates the p52/RelB complex. The p52/RelB complex is imported into the nucleus where it also acts as a transcription factor and activates gene transcription.

Increased expression and/or activity of an NFκB pathway includes overexpression or hyperactivity of any component of an NFκB pathway. Overexpression and/or hyperactivity of the NFκB pathways is well known to cause many adverse conditions. These include, for example, cancer, autoimmune diseases, inflammatory diseases, diabetes, cardiovascular diseases, and neurological diseases. Cancer includes but is not limited to ovarian cancer, breast cancer, prostate cancer, colon cancer, liver cancer, brain cancer, kidney cancer, lung cancer, leukemia, lymphoma, multiple myeloma, thyroid cancer, bone cancer, esophageal cancer, and pancreatic cancer. Inflammatory diseases include but are not limited to arthritis, rheumatoid arthritis, atherosclerosis, multiple sclerosis, asthma, inflammatory bowel disease, Crohn's disease, gastritis, pancreatitis, systemic inflammatory response syndrome, and chronic inflammatory demyelinating polyradiculoneuritis.

NFκB selective inhibitors can be used for cancer prevention and treatment. The relationship between NFκB activation and inflammation-associated cancer have been demonstrated using several mouse models. NFκB activation has been implicated in inflammation associated liver, prostate and colon cancer induction in humans and mouse models. Several antioxidants having electrophilic capacity such as cyclopentenone prostaglandins, dimethoxylsulfoxide, glutathione and non-steroidal anti-inflammatory drugs (NSAIDs) Ibuprofen, sulindac, as well as curcumin inhibit NFκB activity but do not show high selectivity. Aspirin, sulfasalazine, SC-514, and PS-1145 also inhibit NFκB by interrupting phosphorylation of IKK.

Compounds of Formula I display high selectivity for growth inhibition and/or induction of apoptosis in cancer cells, e.g., in ovarian cancer cells.

The disclosed methods include methods for treating disease or disorder capable of being modulated by inhibition of the NFκB pathway, e.g., cancer, comprising administering to a subject a compound that binds a component of the NFκB pathway. In some examples, the compound disrupts binding of a protein which activates the NFκB pathway. In one example, the method includes use of a compound that disrupts binding of a protein to TNFα. In another example, the method includes use of a compound that disrupts binding of a protein to IKKβ. In another example, the compound prevents translocation of NFκB to the nucleus.

Provided herein is a method of modulating the NFκB pathway in a cell, comprising contacting the cell with a compound or a composition as disclosed herein (e.g., the compounds of Formula I or as shown in Table I) in an amount sufficient to modulate the NFκB pathway. The contacting of the cell can occur in vitro or in vivo. In some cases, contacting of the cell occurs in vitro. In other cases, contacting of the cell occurs in vivo. Therefore, the disclosure includes administering one or more of a compound described herein to a subject, such as a human, in need thereof. In some embodiments, the subject suffers from a disease or disorder associated with aberrant activity of the NFκB pathway. Disorders associated with aberrant activity of the NFκB pathway include, but are not limited to, cancer (e.g., ovarian cancer), autoimmune diseases, inflammatory diseases, diabetes, cardiovascular diseases, and neurological diseases. Specifically contemplated cancers include ovarian cancer, breast cancer, prostate cancer, colon cancer, liver cancer, brain cancer, kidney cancer, lung cancer, leukemia, lymphoma, multiple myeloma, thyroid cancer, bone cancer, esophageal cancer, and pancreatic cancer.

The disclosed methods utilize compounds that inhibit the NFκB pathway, for treating, e.g., cancer. Methods for assessing the usefulness of a compound for treating cancer are known to those of skill in the art. For example, compounds may be assessed using models of cancer, including cells (such as ovarian cancer cells), animal models (such as mouse xenograph or other cancer models), or in human subjects having, e.g., ovarian cancer.

The compounds described herein can be used to decrease or prevent cancer in human subjects with e.g., ovarian cancer. In a particular example, a compound or mixture is administered orally, such as by mixing with distilled water. In another example, a test compound or mixture is administered intravenously, such as in saline or distilled water. In some examples, treatment with test compound may be a single dose or repeated doses. The test compound may be administered about every 6 hours, about every 12 hours, about every 24 hours (daily), about every 48 hours, about every 72 hours, or about weekly. Treatment with repeated doses may continue for a period of time, for example for about 1 week to 12 months, such as about 1 week to about 6 months, or about 2 weeks to about 3 months, or about 1 to 2 months. Administration of a compound may also continue indefinitely. Doses of test compound are from about 0.1 mg/kg to about 400 mg/kg, such as about 1 mg/kg to about 300 mg/kg, about 2 mg/kg to 200 mg/kg, about 10 mg/kg to about 100 mg/kg, about 20 mg/kg to about 75 mg/kg, or about 25 mg/kg to about 50 mg/kg.

It will be understood that the methods and compositions described herein for treating cancer, comprising administering a compound that inhibits the NFκB pathway, are applicable to methods of treating other diseases related to NFκB activity, such as those described above. The methods for assessing the effectiveness of test compounds for treating such diseases in cells, appropriate animal models, or affected subjects are known to one of skill in the art.

Uses of the compounds disclosed herein in the preparation of a medicament for treating diseases or disorders related to NFκB activity also are provided herein.

The disclosure herein will be understood more readily by reference to the following examples, below.

EXAMPLES

The following examples are provided for illustration and are not intended to limit the scope of the disclosure.

Synthetic procedures for compounds of Formula I

General Experimental Procedures. All reagents were purchased from commercial sources and were used without further purification. Flash chromatography was carried out on silica gel (200-400 mesh). Thin layer chromatography (TLC) was performed on pre-coated EMD silica gel 60 F254 plates and observed under UV light at 254 nm and analyzed with basic potassium permanganate staining. Column chromatography was performed with silica gel (230-400 mesh, grade 60, Fisher scientific, USA). $^1$H NMR (500 MHz) and $^{13}$C NMR (125 MHz) spectra were recorded in chloroform-d or DMSO-d6 on a Varian-500, Varian-600 and Bruker-500 spectrometer (DMSO-d6 2.50 ppm for 1H and 39.00 ppm for 13C and CDCl3 was 7.26 ppm for 1H and 77.00 ppm for 13C. Proton and carbon chemical shifts were reported in ppm relative to the signal from residual solvent proton and carbon. The purity of all final compounds was 95% as determined by analytical HPLC on a reverse-phase column (Zorbax 300SB C18, 2.1×150 mm, 5 pm particle size) using an Agilent 1200 series system with UV detector (214 nm and 254 nm) using a binary water/acetonitrile containing system 0.1% trifluoracetic acid (TFA) as eluent. Analytical HPLC was carried out on a 250×4.60 mm C-18 column using gradient conditions (10-100% B, flow rate=1.0 mL/min, 15 min). The eluents used were: solvent A (H$_2$O with 0.1% Formic acid) and solvent B (CH$_3$CN with 0.1% formic acid).

Example 1: Compounds of Formula (I) Having an Alkylene Linker.

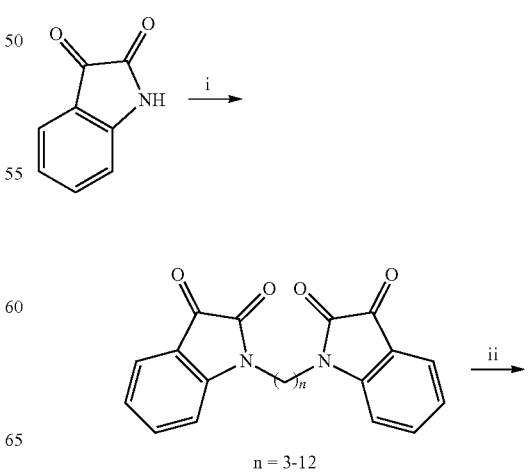

n = 3-12

-continued

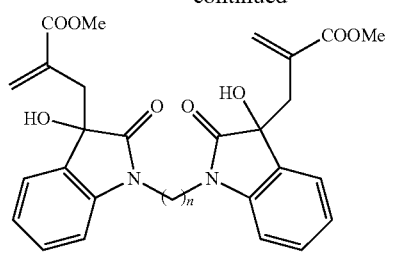

n = 3-12

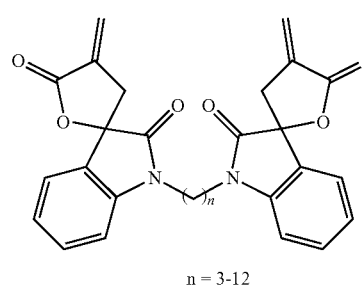

n = 3-12

Step i

Isatin (1 equivalent) and dry DMF were combined in a dry round bottom flask. The reaction mixture was cooled to 0° C., and then NaH (0.45 equivalent) was added. The reaction mixture was stirred for 15 minutes, and then 1,n-dibromoalkane (0.45 equivalent) was added. The reaction was warmed to room temperature and stirred for 24 hours. The crude mixture was diluted in ethyl acetate and washed with ammonium chloride and brine. The organic layer was separated and dried with magnesium sulfate, filtered, and then evaporated to give the pure intermediate compound.

Step ii

In a dry round bottom flask was dissolved isatin (1 equivalent) in THF: water (3:2), followed by addition of indium metal powder (2.2 equivalents). The reaction mixture was stirred for 10 minutes, and then methyl 2-(bromomethyl) acrylate (2.2 equivalents) was added. The reaction mixture was stirred for 24 hours and the progress of the reaction was monitored by thin layer chromatography using 70% ethyl acetate in hexane solvent. Following reaction completion, the reaction mixture was diluted with ethyl acetate and washed with 0.1% HCl, followed by brine, and dried over magnesium sulfate. The crude mixture was purified by column chromatography using a hexane and ethyl acetate gradient to obtain the desired acyclic intermediate compound.

Step iii

In a round bottom flask was dissolved the acyclic intermediate compound (1 equivalent) in dry dichloromethane. The reaction mixture was cooled to 0° C. followed by addition of p-toluenesulfonic acid monohydrate salt (2.2 equivalents). The reaction mixture was stirred at room temperature for 12 hours under inert atmosphere. Completion of the reaction was monitored by thin layer chromatography. The crude mixture was washed with brine and extracted using dichloromethane, dried over magnesium sulfate, and purified via column chromatography using hexane and ethyl acetate gradient to obtain the desired product.

Example 2: 1', 1'''-(heptane-1,7-diyl)bis(4-methyl-3,4-dihydro-5H-spiro[furan-2,3-indoline]-2',5-dione).

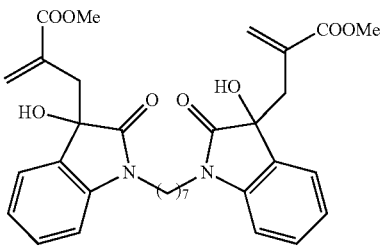

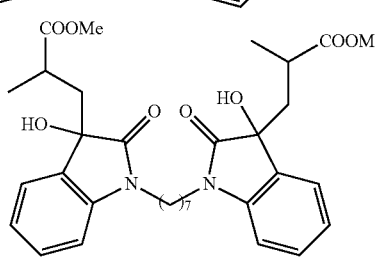

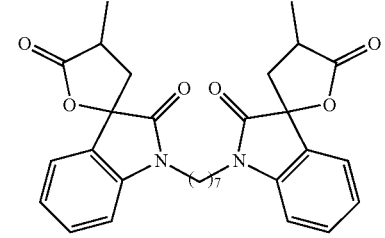

Step i: Dimethyl 2,2'-((heptane-1,7-diylbis(3-hydroxy-2-oxoindoline-1, 3-diyl))bis(methylene))diacrylate To dimethyl 2,2'-((heptane-1,7-diylbis(3-hydroxy-2-oxoindoline-1, 3-diyl))bis(methylene))diacrylate (1 equivalent) in a round bottom flask was added dry THF via syringe. To the reaction mixture was added Pd/C (5% by weight on activated carbon), and nitrogen gas was bubbled though the reaction mixture for about 10 minutes. The reaction mixture was gently vacuumed and was kept under hydrogen atmosphere for 24 hours. After completion, the mixture was passed through a bed of celite and purified by column chromatography using hexane and ethyl acetate gradient to obtain the product, dimethyl 2,2'-((heptane-1,7-diylbis(3-hydroxy-2-oxoindoline-1, 3-diyl))bis(methylene)) diacrylate.

Step ii: 1',1'''-(heptane-1,7-diyObis(4-methyl-3,4-dihydro-5H-spiro[furan-2,3'-indoline]-2',5-dione)

A round bottom flask was charged with dimethyl 2,2'-((heptane-1,7-diylbis(3-hydroxy-2-oxoindoline-1, 3-diyl)) bis(methylene)) diacrylate (1 equivalent) and dry dichloromethane. The reaction mixture was cooled to 0° C. followed by addition of p-toluenesulfonic acid monohydrate salt (1.2 equivalents). The reaction mixture was stirred at room temperature for 12 hours under inert atmosphere. Completion of the reaction was monitored by thin layer chromatography. The crude mixture was washed with brine and extracted using dichloromethane, dried over magnesium sulfate, and purified via column chromatography using hexane and ethyl acetate gradient to yield the title compound.

Example 3: 1,1''-(octane-1,8-diyl)bis(4,7-dimethyl-4'-methylenespiro[indoline-3, 2'-pyrrolidine]-2,5'-dione).

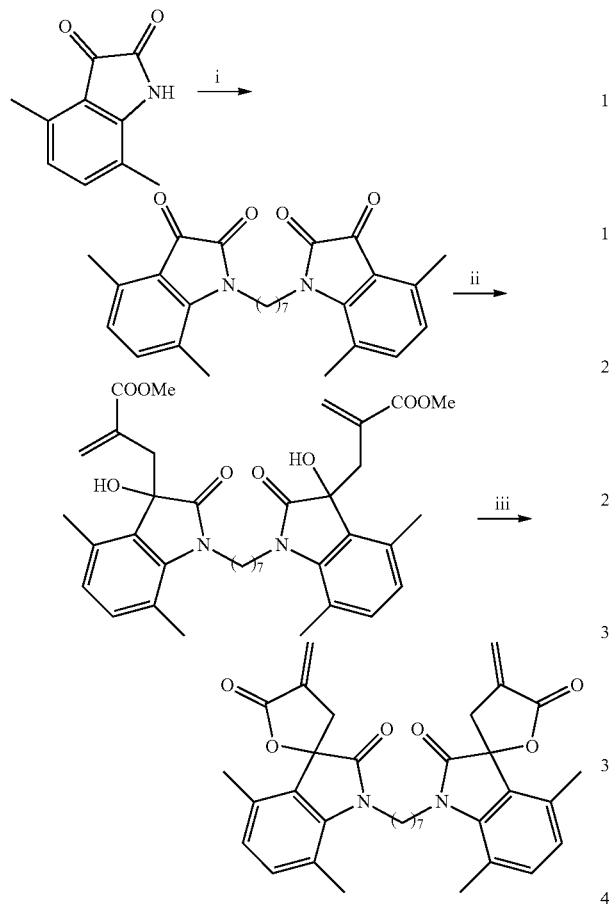

Step i: 1,1'-(heptane-1,7-diyObis(4,7-dimethylindoline-2,3-dione)

In a dry round bottom flask were combined 4,7-dimethylindoline-2,3-dione (1 equivalent) and dry DMF. The reaction mixture was cooled to 0° C., followed by addition of NaH (0.45 equivalent). The reaction mixture was stirred for 15 minutes followed by addition of 1,3-dibromoalkane (0.45 equivalents). The reaction was warmed to room temperature and stirred at room temperature for 24 hours. The crude mixture was diluted in ethyl acetate and washed with ammonium chloride followed by brine. The organic layer was separated and dried with magnesium sulfate, filtered, and evaporated to yield the desired product.

Step ii: dimethyl 2,2'-((heptane-1,7-diylbis(3-hydroxy-4, 7-dimethyl-2-oxoindoline-1, 3-diyl))bis(methylene))diacrylate In a dry round bottom flask were combined 1,1'-(heptane-1,7-diyl)bis(4, 7-dimethylindoline-2,3-dione) (1 equivalent) and THF: water (3:2), followed by addition of indium metal powder (2.2 equivalents). The reaction mixture was stirred for 10 minutes followed by addition of methyl 2-(bromomethyl) acrylate (2.2 equivalents). The reaction mixture was stirred for 24 hours and the progress of the reaction was monitored by thin layer chromatography using 70% ethyl acetate in hexane solvent. Following reaction completion, the reaction mixture was diluted with ethyl acetate and washed with 0.1% HCl, followed by brine, and dried using magnesium sulfate. The crude mixture was purified by column chromatography using a hexane and ethyl acetate gradient to yield the desired product.

Step iii: 1,1''-(heptane-1,7-diyObis(4,7-dimethyl-4'-methylenespiro[indoline-3,2'-pyrrolidine]-2, 5'-dione)

Dimethyl 2,2'-((heptane-1,7-diylbis(3-hydroxy-4,7-dimethyl-2-oxoindoline-1, 3-diyl))bis(methylene))diacrylate (1 equivalent) was dissolved in dry dichloromethane in a round bottom flask. The reaction mixture was cooled to 0° C., followed by addition of p-toluenesulfonic acid monohydrate salt (2.2 equivalents). The reaction mixture was stirred at room temperature for 12 hours under inert atmosphere. Completion of the reaction was monitored by thin layer chromatography. The crude mixture was washed with brine and extracted using dichloromethane, dried over magnesium sulfate, and purified by column chromatography using a hexane and ethyl acetate gradient to yield the title compound.

Example 4: 1,1''-(1,4-phenylenebis(methylene))bis(4'-methylenespiro[indoline-3, 2'-pyrrolidine]-2,5'-dione).

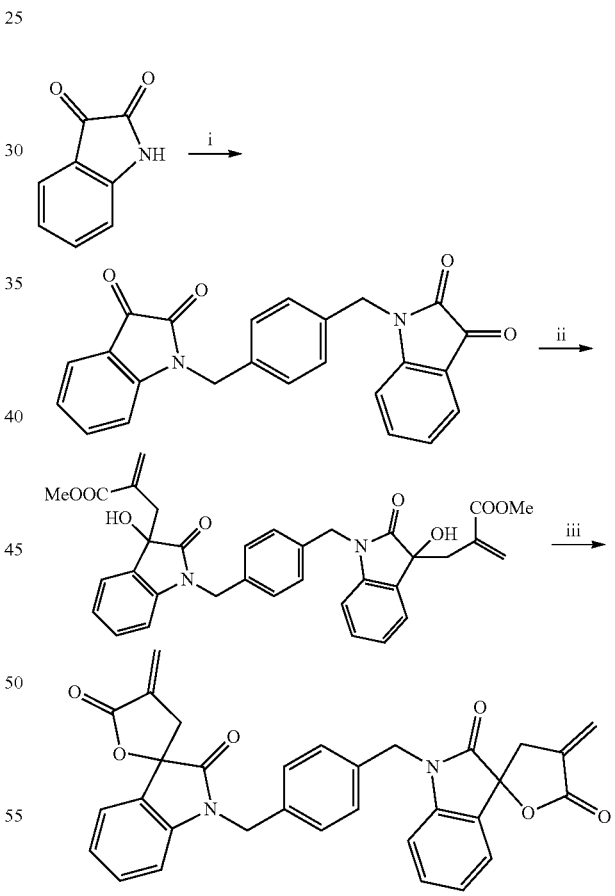

Step i: 1,1'-(1,4-phenylenebis(methylene))bis(indoline-2,3-dione)

In a dry round bottom flask were combined isatin (1 equivalent) and dry DMF. The reaction mixture was cooled to 0° C. followed by addition of NaH (0.45 equivalents). The reaction mixture was stirred for 15 minutes followed by addition of 1,4-bis(bromomethyl)benzene (0.45 equivalents). The reaction was warmed to room temperature and stirred for 24 hours. The crude mixture was diluted in ethyl acetate and washed with ammonium chloride, followed by brine. The organic layer was separated and dried with magnesium sulfate, filtered, and evaporated to give the desired compound.

Step ii: dimethyl 2,2'-(((1,4-phenylenebis(methylene))bis (3-hydroxy-2-oxoindoline-1, 3-diyl))bis(methylene))diacrylate In a dry round bottom flask were combined 1,1'-(1,4-phenylenebis(methylene))bis(indoline-2, 3-dione) (1 equivalent) and THF: water (3:2), followed by addition of indium metal powder (2.2 equivalents). The reaction mixture was stirred for 10 minutes followed by addition of methyl 2-(bromomethyl) acrylate (2.2 equivalents). The reaction mixture was stirred for 24 hours and progress of the reaction was monitored by thin layer chromatography using 70% ethyl acetate in hexane solvent. Following completion of the reaction, the mixture was diluted with ethyl acetate and washed with 0.1% HCl, followed by brine, and dried over magnesium sulfate. The crude mixture was purified by column chromatography using a hexane and ethyl acetate gradient to yield the desired compound.

Step ii: 1,1''-(1,4-phenylenebis(methylene))bis(4'-methylenespiro[indoline-3,2'-pyrrolidine]-2, 5'-dione)

Dimethyl 2,2'-(((1,4-phenylenebis(methylene))bis(3-hydroxy-2-oxoindoline-1, 3-diyl))bis(methylene))diacrylate (1 equivalent) was dissolved in dry dichloromethane in a round bottom flask. The reaction mixture was cooled to 0° C. followed by addition of p-toluenesulfonic acid monohydrate salt (2.2 equivalents). The reaction mixture was stirred at room temperature for 12 hours under inert atmosphere. Completion of the reaction was monitored by thin layer chromatography. The crude mixture was washed with brine and extracted using dichloromethane, dried over magnesium sulfate, and purified by column chromatography using a hexane and ethyl acetate gradient to yield the title compound.

Biological assay data

Example 5: Cell Viability Assay.

MiaPaCa2, A2780, and OVCAR5 cells were plated at 4000 cells/well in a 96-well plate and allowed to adhere overnight. The following day, cells were treated with compounds using ~10-fold dilutions starting at 1000 nM. PrestoBlue reagent (Invitrogen #A13262) was added to cells after 72 hour drug incubation to assess the growth inhibition. Fluorescence excitation/emission was measured at 560/590nM using a SpectraMax M5$^e$ instrument. Growth inhibition was calculated using $100-[100*(Samples-T_0)/(T_{100}-T_0)]$. $T_0$ is the vehicle control reading immediately following drug addition and $T_{100}$ is the control reading at the end of 72 hour incubation. Results are presented in Table 2, below.

TABLE 2

| Compound # | IC$_{50}$ (µM) | | |
|---|---|---|---|
| | A2780 | OVCAR5 | MiaPaCa2 |
| 25-4 | 0.99 ± 0.11 | 3.13 ± 0.55 | 6.08 |
| 40-059 | 0.42 ± 0.04 | 0.32 ± 0.02 | |
| 36-286 | 0.23 ± 0.02 | 0.09 ± 0.01 | |
| 40-038 | 0.40 ± 0.06 | 0.20 ± 0.04 | |
| 36-202 | 0.29 ± 0.04 | 0.09 ± 0.01 | 0.91 |
| 36-239 | 0.70 ± 0.09 | 0.30 ± 0.02 | 1.05 |
| 36-252 | 0.32 | 0.32 | 0.76 |
| 36-254 | 0.60 ± 0.07 | 0.32 | 1.70 |

TABLE 2-continued

| Compound # | IC$_{50}$ (µM) | | |
|---|---|---|---|
| | A2780 | OVCAR5 | MiaPaCa2 |
| 36-204 | 1.08 ± 0.01 | 0.48 ± 0.06 | 2.16 |
| 36-256 | 0.49 ± 0.06 | 0.41 ± 0.06 | 1.47 |
| 36-258 | 0.77 ± 0.14 | 0.83 ± 0.12 | |
| 36-242 | 0.50 ± 0.06 | 0.47 ± 1.29 | 1.94 |
| 40-014 | 0.31 ± 0.02 | 0.18 ± 0.01 | |
| 36-280 | 0.35 ± 0.05 | 0.37 ± 0.04 | |
| 36-297 | Inactive | Inactive | |

Example 6: Cell-based growth inhibition and apoptosis assays.

The in vitro activity of the dimers was assessed through cell-based assays to determine their ability to selectively inhibit growth and induce apoptosis in ovarian cancer cells. In a 3-day growth assay, compound 36-242 was shown to be 10-fold more potent than monomeric compound 19. In the same assay, reduced compound 36-297.

In a panel of high grade serous carcinoma (HGSC) ovarian cancer cell lines, the dimer with the 7-carbon linker 36-252 (sub µM) was more potent than analog 19 and a dimer with a 12-carbon linker 36-242. The IC$_{50}$ value of all three inhibitors was greater than 20 µM in this cell line. The average IC$_{50}$ value of 36-252 in HGSC cell lines was 0.78 µM, demonstrating that 36-252 inhibits growth of HGSC (efficacy) with greater than 25-fold selectivity over nontransformed cell line (toxicity), corresponding to an apparent therapeutic index of >25.

Monomeric compound 19, 36-252, and 36-242 were evaluated in non-transformed HGSC precursor fallopian tube epithelial (FTE) cells FT282. Unlike HGSC cell lines the IC$_{50}$ values of the inhibitors in the FT282 cells were greater than 20 µM, which is 25-fold better than the average IC$_{50}$ value (0.78 µM) of 36-252 in HGSC cell lines.

Example 7: Caspase and kB-Luciferase Assays.

To determine the effect of 36-252 on apoptosis, a small panel of HGSC cell lines was treated with 1 µM 36-252 for 6 hours (1 µM of flavopiridol was used as a positive control). Caspases are a class of cysteine proteinases that are activated during apoptosis and measuring caspase activity is routinely used to detect activation of apoptotic signaling. Activation of caspase 3/7 was assessed using a luciferase assay. Increased caspase 3/7 activity was seen in three of the five HGSC cell lines.

2500 cells were plated in a 384-well black walled clear bottom plate at 2,500 cells per well in 100 µL per well in the presence of 4.5 µM doxycycline. Cells were incubated overnight to adhere to plate. Cells were then treated at concentrations indicated in FIG. 1. After cells were treated and plate was allowed to incubate, Caspase-glo (Promega G8093) reagent was added and the plate was allowed to incubate for 30 min. The plate was then read for luminescence at 1000 ms. Presto-blue was added at a volume of 1/10 total volume per well (2.5µL) and cells were allowed to incubate for 10 min. The plate was then read for fluorescence at 560$_{ex}$/590em. Values were calculated by: ([Luminescence*100]/Fluorescence)/DMSO$_{avg}$.

Figure 3:
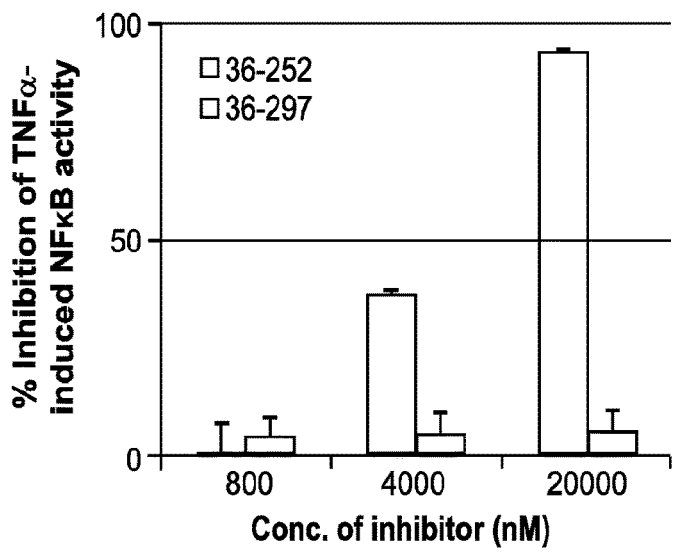
FIG. 3 shows the effect of compounds 36-252 and 36-297 on cancer cells (A549 luciferase cells) as measured by inhibition of TNF-α-induced NFκB activity.
Figure 4:
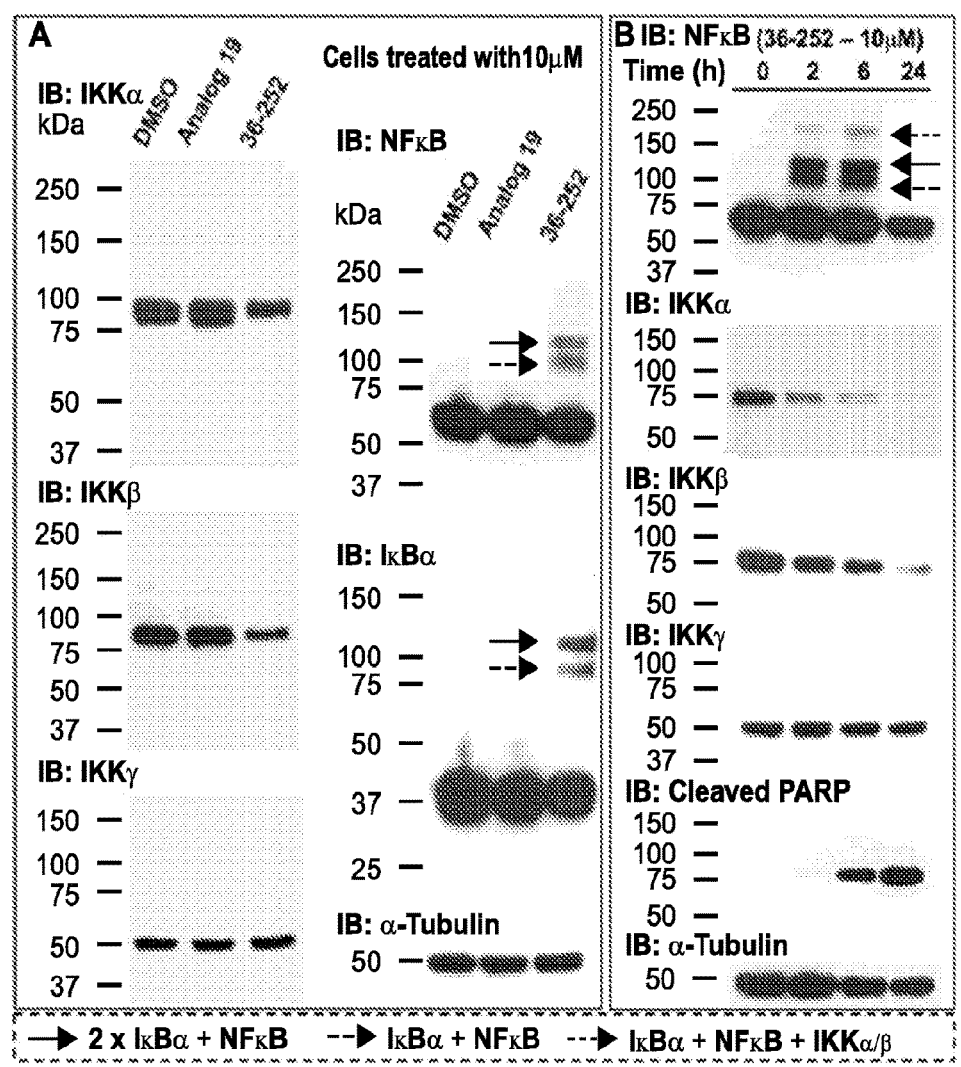
FIG. 4 shows the results of a Western blot analysis to determine crosslinking of proteins in the IKK complex.
Figure 5:
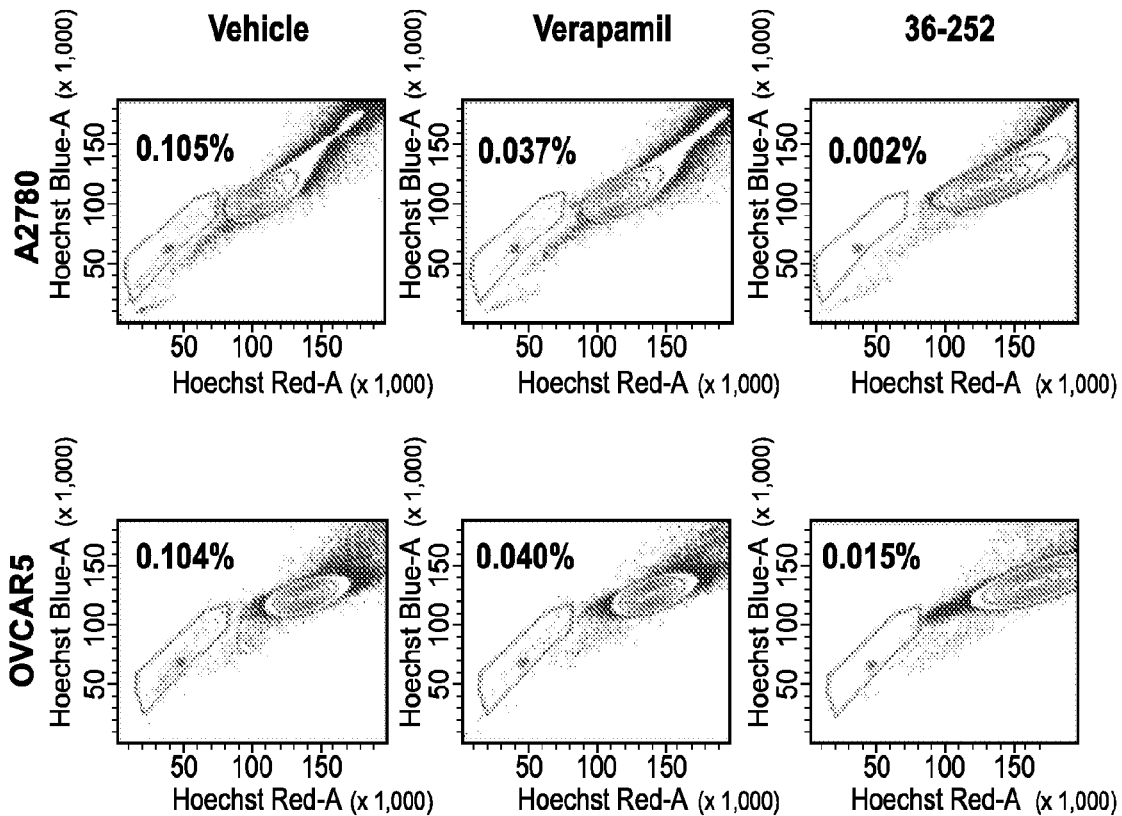
FIG. 5 shows the results of a side population analysis in OVCAR-5 or A2780 cells.
Figure 6:
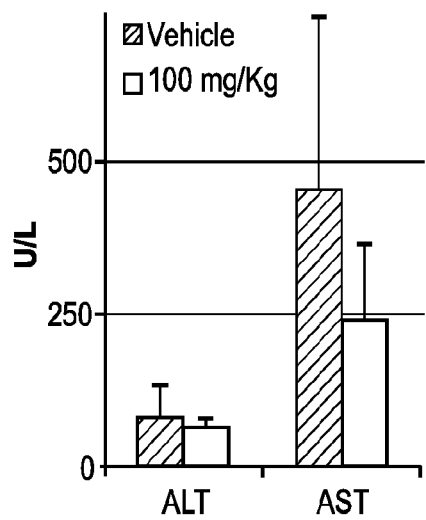
FIG. 6 shows the results of a toxicity study comparing the effects of DMSO vs. 100 mg/kg 36-252 on aspartate transaminase (AST) and alanine transaminase (ALT) in mice.
Figure 7:
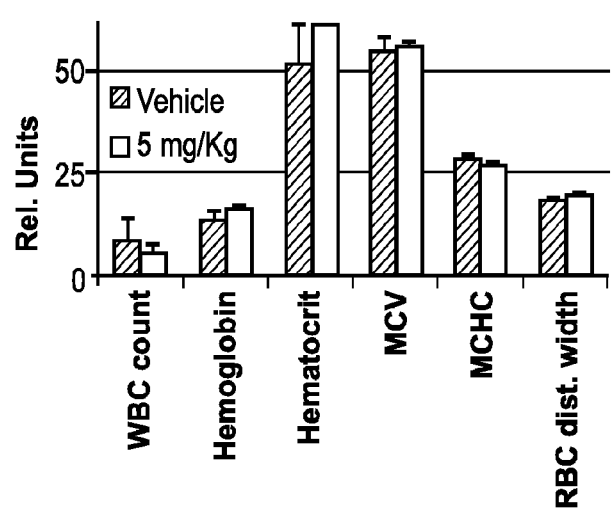
FIG. 7 shows the results of hematological analysis in control (DMSO) vs. 36-252-treated mice.

A549 luciferase cells were seeded in white 96-well plates at a density of 50,000 cells per well and incubated overnight. Cells were then treated with the compound concentrations indicated in FIG. 3 for 2 hours. Cells were stimulated with 20 ng/mL TNFα (Panomics) for 3 hours. AlamarBlue (abSerotec) was added (which served as a control for seeding and viability) and the cells were incubated for 3 additional hours. ONE-Glo Luciferase reagent (Promega) was added to each well and cells were incubated at room temperature for an additional 10 minutes before luminescence was measured at 1000 ms integration on a SpectraMax M5e plate reader.

The effect 36-252 and 36-297 on NFκB driven gene expression was evaluated using a cancer cell line specifically designed to monitor the activity of NFκB in response to TNF-α. Cells were seeded onto 96-well plates and allowed to attach overnight. The cells were treated with 36-252 and 36-297 (20, 4, and 0.8 pM) for 2 hours, followed by TNF-a for an additional 6 hours. Under multiplexing conditions the cells were assayed for viability using Alamar Blue (Ab Serotec) and the NFκB transcription activity using the ONE-Glo luciferase system (Promega). Dose-dependent inhibition was observed with 36-252 and not 36-297, which demonstrates the need for the Michael acceptor in 36-252 to inhibit NFκB mediated gene expression.

Example 8: Western Blot Analyses.

Crosslinking of proteins in the IKK complex was studied as follows. A2780 cells were treated with 10 pM of analog 19 or 36-252 and incubated for 2 hours. High molecular weight bands in the NFκB and IKBα blots were observed, indicating that crosslinking had occurred. A time course study with 36-252 showed a band between 150 and 250 kDa in addition to the IKBα-NFκB bands, corresponding to a possible IKBα-NFκB-IKKα/β complex resulting in degradation of IKK α/β and PARP cleavage.

Cells were washed with cold 1×PBS 3 times and scraped before being lysed by a buffer containing the following: 50 mM Tris, 100 mM NaCl, 1% NP-40, 2nM EDTA, 20% SDS, 20×PPl (Na$_3$VO$_4$, NAF, β-glycerophosphate) and 1 mmol/L PMSF. After collection, samples were incubated on ice for 30 minutes and vortexed in 15 minute intervals. Samples were then centrifuged at 14,000rpm for 10 minutes at 4° C. and supernatant was collected. Protein quantification was determined by BCA Protein Assay (Pierce #23225). 20-40ug protein samples were run on 4-15% gradient gels (BioRad) in 1×TRIS-Glycine-SDS Buffer (Research Products International Corporation #T32080) at 120V for ~60 minutes and separated by SDS-page electrophoresis. Samples were transferred to a PVDF membrane by semi-dry transfer method (ThermoScientific #35035) run at 18V for ~35 minutes. Membranes were blocked in 5% milk diluted in 1×-Tris Buffered Saline with 0.1% Tween (1×TBST) for 1 hour at room temperature rocking at low speed. Primary antibodies were diluted in 5% milk in 1×TBST and were rocked gently overnight in 4° C. Membranes were incubated with the appropriate HRP-conjugated secondary antibody for 1 hour at room temperature while gently rocking. 3 washes (10 minute) with 1×TBST occurred before and after secondary antibody. ECL Prime (GE Healthcare #RPB2236) was used to detect protein expression Example 9: Side Population Analysis.

Cancer cells with the ability to efflux Hoechst 33342 dye are termed "side population" (SP). SP cells are far more tumorigenic because they contain a sub-population of cells with cancer stem-like properties A majority of ovarian cancer patients relapse and become drug resistant which has been attributed to the inability to kill stem cells enriched in the SP. The effects of 36-252 and Verapamil (positive control) on the side population in ovarian cancer cell lines (A2780 and OVCAR5) by analyzing the fluorescent profile using flow cytometry methods. While Verapamil eliminated about 60% of SP cells in both cell lines, 36-252 eliminated >85% of OVCAR5 SP cells and >98% of A2780 SP cells.

2 million OVCAR-5 or A2780 cells were treated with 60 µM of verapamil, or 36-252 and vehicle control for 15 min at 37° C. Hoechst 33342 dye (5 µg) was added to each tube and incubated for 45 min at 37° C. Tubes were vortexed slightly after every 5 min. Cells were resuspended in a single cell suspension after centrifugation and kept on ice before acquisition. The side-population was measured by flow cytometry.

Example 10: Dose limiting toxicities.

Six to eight-week-old C57 Albino mice (18-22 grams) were used in this study and were randomly assigned. For MTD studies, 3 mice were randomly assigned to six groups. Animals (Group 1-6) received a single dose of (0, 1, 5, 10, 20 and 100 mg/Kg in 30 mL neat DMSO) of 36-252 via intraperitoneal injection. Mice were sacrificed after 48 hours, and blood and serum samples were subjected to hematology and clinical chemistry analyses. For group 7, a 6-day, 5 mg/kg/day study was carried out followed by submission of samples for hematology and clinical chemistry analyses. Cohort summaries are presented in Table 3, below.

TABLE 3

| Grp | Dose (mg/Kg) | No. of doses | Treated/ Alive |
| --- | --- | --- | --- |
| 1 | Vehicle | 1 | (3/3) |
| 2 | 1 | 1 | (3/3) |
| 3 | 5 | 1 | (3/3) |
| 4 | 10 | 1 | (3/3) |
| 5 | 20 | 1 | (3/3) |
| 6 | 100 | 1 | (3/3) |
| 7 | Vehicle | 7 | (3/3) |
| 8 | 5 | 7 | (3/3) |

In the phase I study, the lethal dose or maximum tolerated dose of 36-252 was evaluated. Even at 100 mg/kg, no sign of overt toxicity was observed. In the phase II study, three mice at 5 mg/kg/day were administered intraperitoneally for six days. No mortality or abnormal clinical levels were observed, nor was any statistical difference in mean body weight observed. Compared to DMSO treated mice, hematological analysis showed no significant differences in relative WBC, RBC, or hemoglobin numbers in 36-252 treated mice.

In view of the many possible embodiments to which the principles of the disclosure may be applied, it should be recognized that the illustrated embodiments are only examples and should not be taken as limiting the scope of the invention.

What is claimed:

1. A compound, or pharmaceutically acceptable salt thereof, having the structure of Formula I:

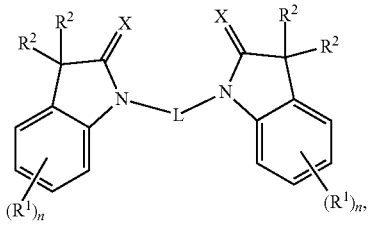

(I)

wherein

X is O, S, or NR$^4$;

L is C$_{1-18}$alkylene or C$_{2-18}$alkenylene optionally interrupted with one or more of (i) non-adjacent heteroatom(s) selected from O, S, and NR$^4$, (ii) C(O)NR$^4$, (iii) C$_{6-10}$aryl, (iv) 5-10 membered heteroaryl having 1-4 heteroatoms selected from N, O, and S, (v) 3-12 membered cycloalkyl ring, and (vi) 3-7 membered heterocycloalkyl ring having 1-3 ring heteroatoms selected from O, S, and N, and said aryl, heteroaryl, cycloalkyl, and heterocycloalkyl are optionally substituted with one or more R$^4$;

each R$^1$ is independently selected from the group consisting of C$_{1-6}$alkyl, halo, CN, N(R$^4$)$_2$, OR$^4$, NO$_2$, CO$_2$R$^4$, (C=O)R$^4$, CON(R$^4$)$_2$, NR$^4$(C=O)R$^5$, C$_{6-10}$aryl, and 5-10 membered heteroaryl having 1-4 heteroatoms selected from N, O, and S, and said alkyl can be optionally substituted with 1 to 3 R$^3$;

two R$^2$ are provided as a pair, together with the carbon atom to which they are attached form a ring having the structure:

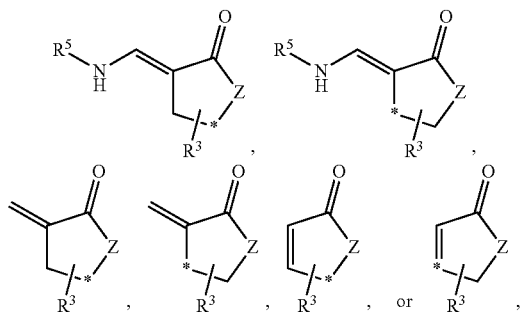

wherein * is the carbon atom to which each R$^2$ is attached, Z is O or NR$^4$, and R$^5$ is C$_{1-6}$alkyl, C$_{2-6}$alkenyl, C$_{6-10}$ aryl, or 3-7 membered heterocycloalkyl ring having 1-3 ring heteroatoms selected from O, S, and N each remaining R$^2$ is independently selected from the group consisting of C$_{1-6}$alkyl, C$_{2-6}$alkenyl, C$_{2-6}$alkynyl, halo, OR$^4$, COR$^4$, CO$_2$R$^4$, CON(R$^4$)$_2$, N(R$^4$)$_2$, and SR$^4$, or a pair of two R$^2$ together with the carbon atom to which they are attached form a saturated or unsaturated 4-8 membered cycloalkyl or heterocycloalkyl ring, wherein the heterocycloalkyl ring has 1 or 2 ring heteroatoms selected from O, S, and N, and wherein said alkyl, alkenyl, alkynyl, cycloalkyl ring, and heterocycloalkyl ring are optionally substituted with 1 to 3 R$^3$, with the proviso that at least one R$^2$ or one pair of two R$^2$ together forming a ring comprise an α,β-unsaturated moiety;

each R$^3$ is independently selected from the group consisting of C$_{1-6}$alkyl, C$_{2-6}$alkenyl, C$_{2-6}$ alkynyl, halo, CN, N(R$^4$)$_2$, OR$^4$, NO$_2$, oxo, =S, =NR$^4$, CO$_2$R$^4$, (C=O)R$^4$, CON(R$^4$)$_2$, C$_{6-10}$aryl, and 5-10 membered heteroaryl having 1-4 ring heteroatoms selected from N, O, and S, and wherein said alkyl, alkenyl, and alkynyl are optionally substituted with 1 to 3 R$^4$;

each R$^4$ is independently selected from the group consisting of H, C$_{1-6}$alkyl, C$_{2-6}$alkenyl, and C$_{2-6}$alkynyl, wherein said alkyl, alkenyl, and alkynyl are optionally substituted with one or more substituents selected from the group consisting of halo, CN, NH$_2$, OH, and C$_{1-6}$alkoxy; and n is 0-4.

2. The compound or salt of claim 1, wherein Z is O or NH.

3. The compound or salt of claim 1, wherein L is selected from the group consisting of uninterrupted C$_{1-18}$alkylene,

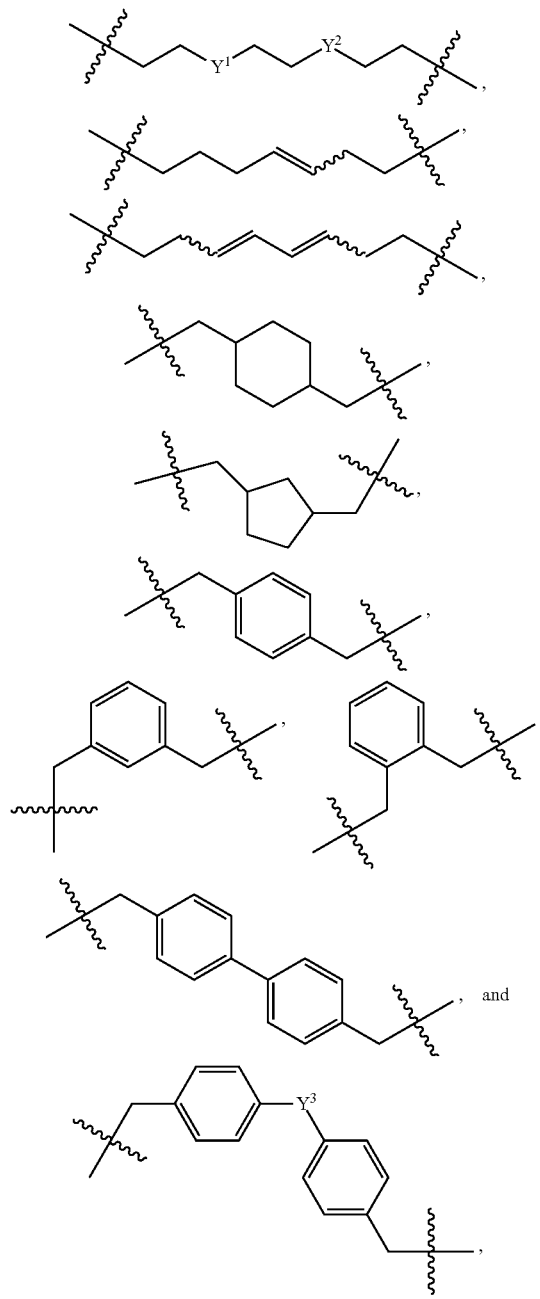

$Y^1$, $Y^2$, and $Y^3$ are each independently O or $NR^4$, and ⌇ indicates that the double bond is cis or trans.

4. The compound or salt of claim 1, wherein L is uninterrupted $C_{1-18}$alkylene.

5. The compound or salt of claim 4, wherein L is
(i) $C_7$alkylene, or
(ii) $C_{12}$alkylene.

6. The compound or salt of claim 3, wherein
(i) at least one of $Y^1$ and $Y^2$ is O, or
(ii) at least one of $Y^1$ and $Y^2$ is $NR^4$.

7. The compound or salt of claim 6, wherein
(i) each of $Y^1$ and $Y^2$ are O, or
(ii) each of $Y^1$ and $Y^2$ are $NR^4$.

8. The compound or salt of claim 3, wherein $R^4$ is H or $C_{1-6}$alkyl.

9. The compound or salt of claim 1, wherein L is $C_{2-18}$alkenylene.

10. The compound or salt of claim 9, wherein L comprises
(i) one carbon-carbon double bond, or
(ii) two carbon-carbon double bonds.

11. The compound or salt of claim 9, wherein L is

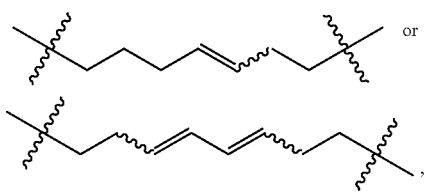 or

, and ⌇ indicates that the double bond is cis or trans.

12. The compound or salt of claim 1, wherein L is

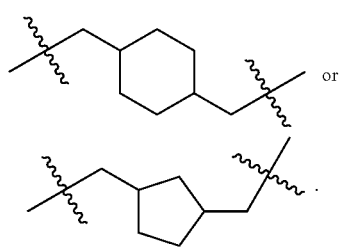.

13. The compound or salt of claim 1, wherein L is $C_{1-18}$alkylene or $C_{2-18}$alkenylene interrupted by at least one phenyl.

14. The compound or salt of claim 3, wherein L is selected from the group consisting of

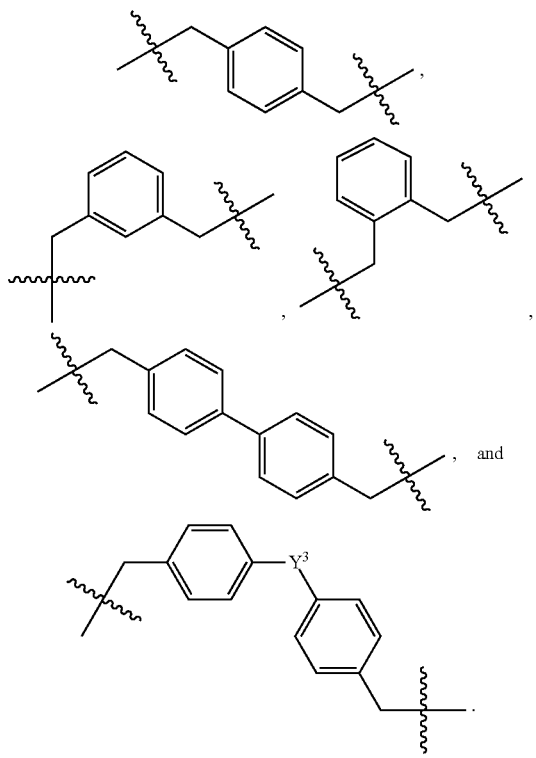, and

.

15. The compound or salt of claim 14, wherein
(i) $Y^3$ is O, or
(ii) $Y^3$ is $NR^4$, wherein $R^4$ is methyl.

16. The compound or salt of claim 1, wherein L is

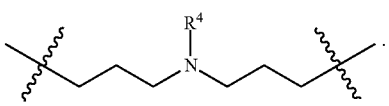.

17. A compound, as recited in Table 1, or a pharmaceutically acceptable salt thereof:

TABLE 1

| Compound # | Structure |
|---|---|
| 40-059 | 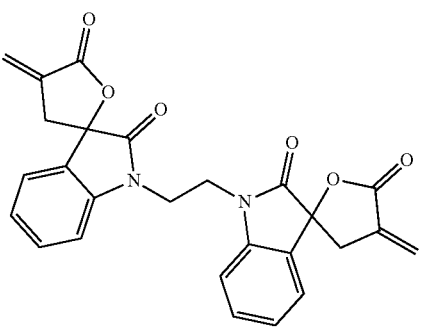 |

TABLE 1-continued

| Compound # | Structure |
|---|---|
| 36-286 | 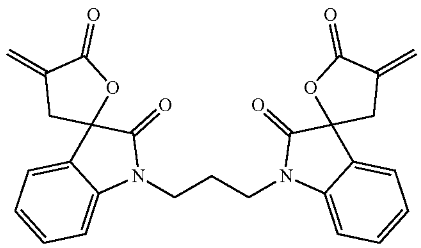 |
| 40-039 | 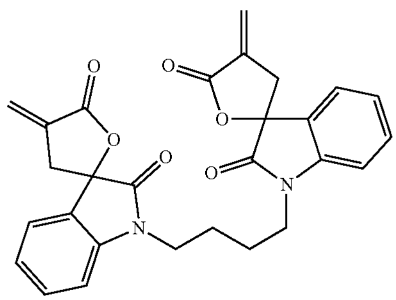 [SMILES: C=C1CC2(OC1=O)C(=O)N(CCCCN1C(=O)C3(CC(=C)C(=O)O3)c3ccccc31)c1ccccc12] |
| 36-202 | 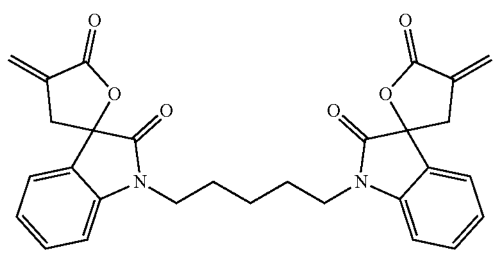 |
| 36-239 | 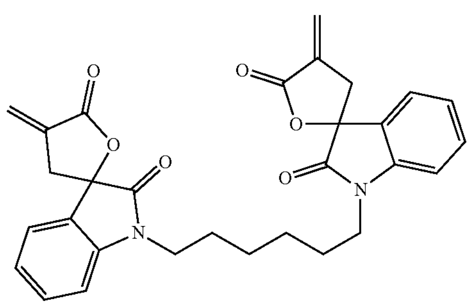 [SMILES: C=C1CC2(OC1=O)C(=O)N(CCCCCCN1C(=O)C3(CC(=C)C(=O)O3)c3ccccc31)c1ccccc12] |
| 36-252 | 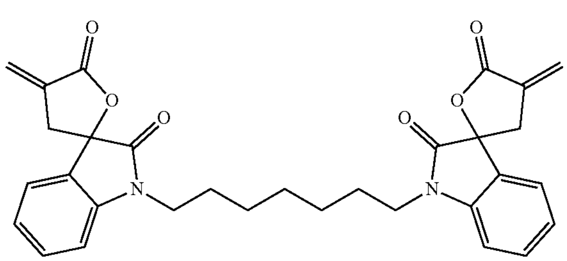 |

TABLE 1-continued

| Compound # | Structure |
|---|---|
| 36-254 | 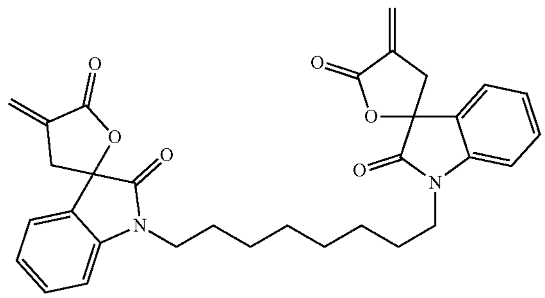 [SMILES: C=C1CC2(OC1=O)C(=O)N(CCCCCCCCN1C(=O)C3(CC(=C)C(=O)O3)c3ccccc31)c1ccccc12] |
| 36-204 | 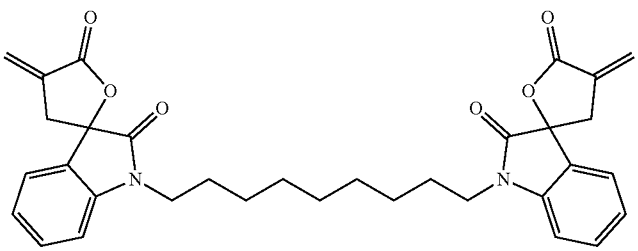 |
| 36-256 | 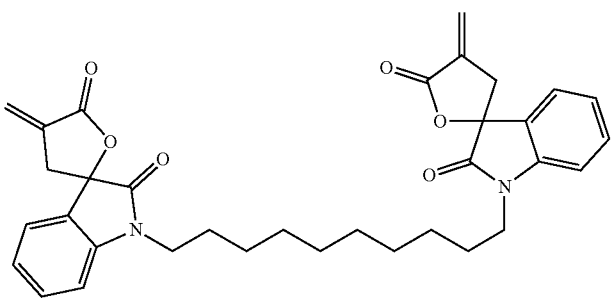 [SMILES: C=C1CC2(OC1=O)C(=O)N(CCCCCCCCCCN1C(=O)C3(CC(=C)C(=O)O3)c3ccccc31)c1ccccc12] |
| 36-258 | 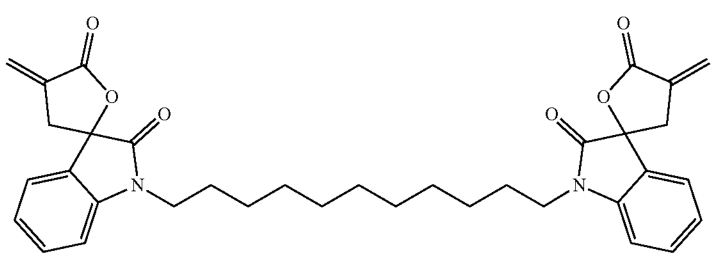 |
| 36-242 | 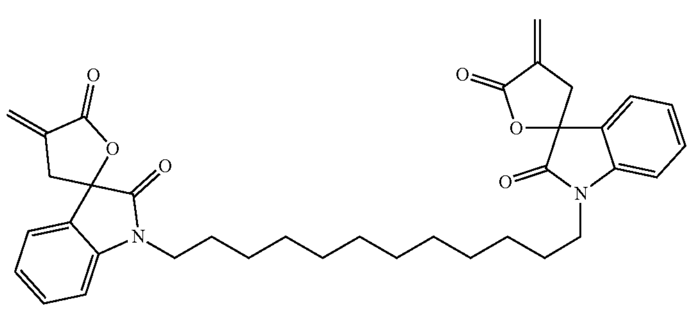 [SMILES: C=C1CC2(OC1=O)C(=O)N(CCCCCCCCCCCCN1C(=O)C3(CC(=C)C(=O)O3)c3ccccc31)c1ccccc12] |

TABLE 1-continued

| Compound # | Structure |
|---|---|
| 36-280 | 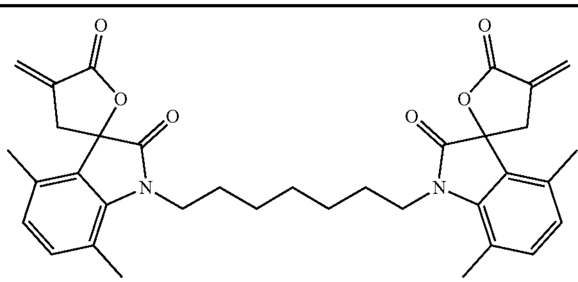 |
| 36-297 | 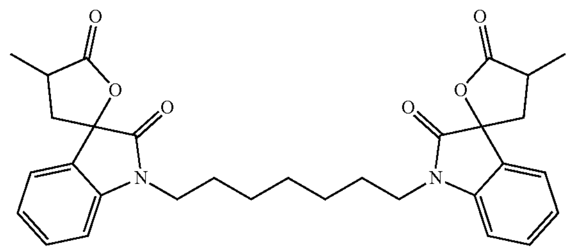 |
| 40-014 | 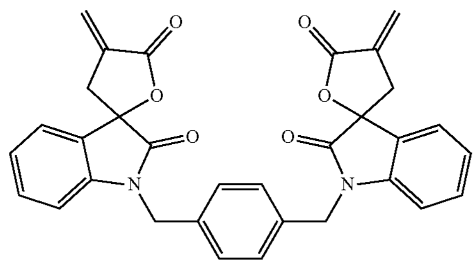 [SMILES: C=C1CC2(OC1=O)C(=O)N(Cc1ccc(CN3C(=O)C4(CC(=C)C(=O)O4)c4ccccc43)cc1)c1ccccc12] |
| 36-252P | 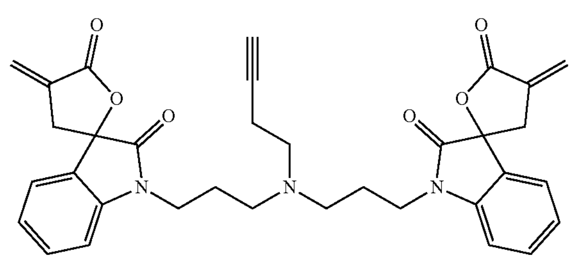 |
| 36-252N | 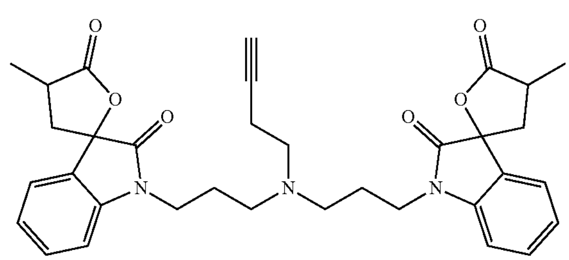 |
| P1 | 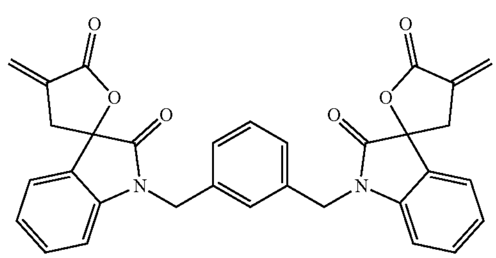 |

TABLE 1-continued

| Compound # | Structure |
|---|---|
| P2 | 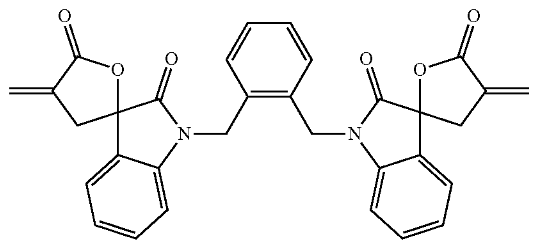 |
| P3 | 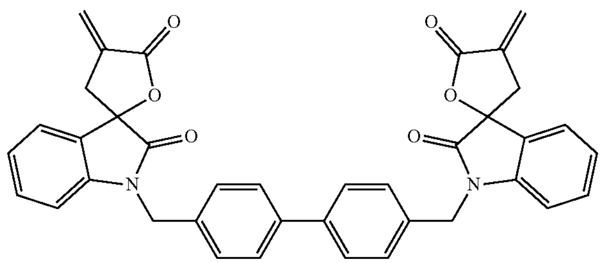 [SMILES: C=C1CC2(OC1=O)C(=O)N(Cc1ccc(-c3ccc(CN4C(=O)C5(CC(=C)C(=O)O5)c5ccccc54)cc3)cc1)c1ccccc12] |
| P4 | 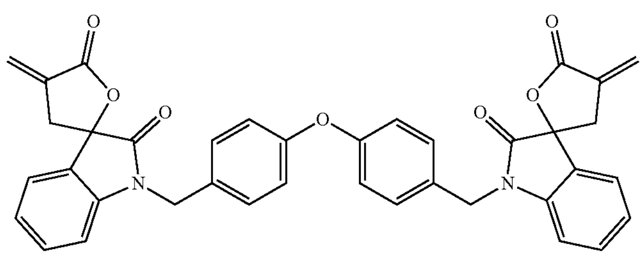 |
| P5 | 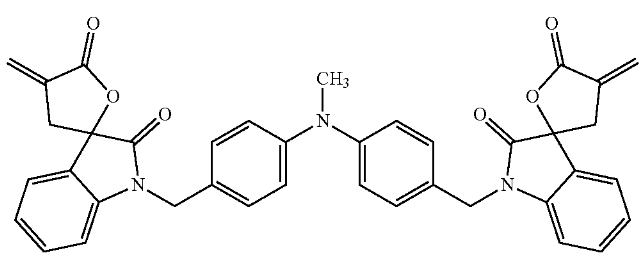 |
| P6 | 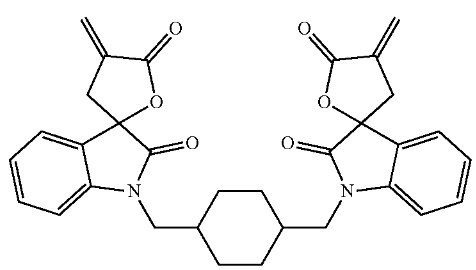 [SMILES: C=C1CC2(OC1=O)C(=O)N(CC1CCC(CN3C(=O)C4(CC(=C)C(=O)O4)c4ccccc43)CC1)c1ccccc12] |
| P7 | 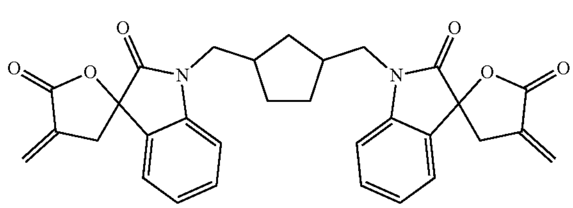 [SMILES: C=C1CC2(OC1=O)C(=O)N(CC1CCC(CN3C(=O)C4(CC(=C)C(=O)O4)c4ccccc43)C1)c1ccccc12] |

TABLE 1-continued
| Compound # | Structure |
|---|---|
| P8 | 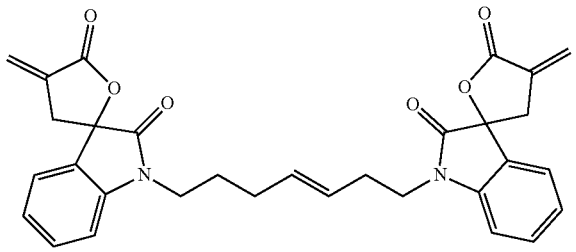 |
| P9 | 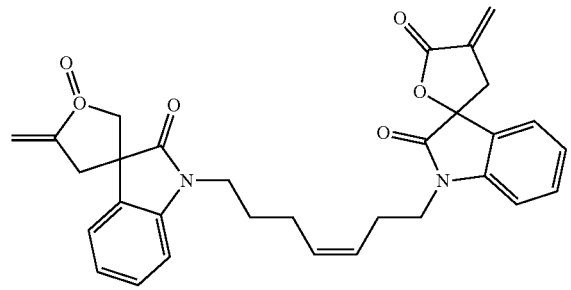 |
| P10 | 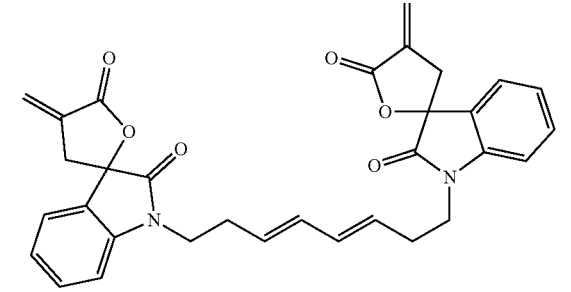 [SMILES: C=C1CC2(OC1=O)C(=O)N(CC/C=C/C=C/CCN1C(=O)C3(CC(=C)C(=O)O3)c3ccccc31)c1ccccc12] |
| P11 | 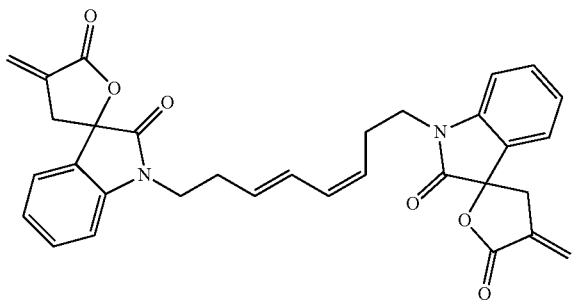 |
| P12 | 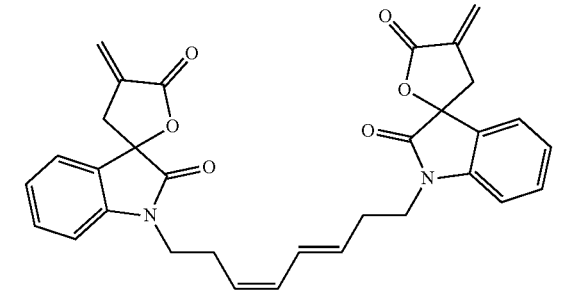 [SMILES: C=C1CC2(OC1=O)C(=O)N(CC/C=C\C=C\CCN1C(=O)C3(CC(=C)C(=O)O3)c3ccccc31)c1ccccc12] |

TABLE 1-continued
| Compound # | Structure |
|---|---|
| P13 | 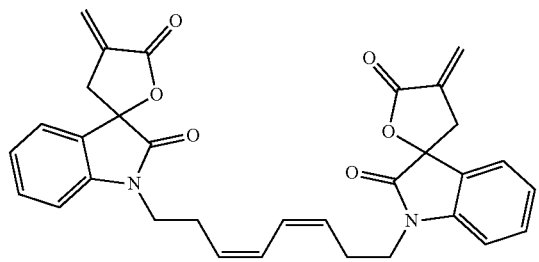 [SMILES: C=C1CC2(OC1=O)C(=O)N(CC/C=C\C=C/CCN1C(=O)C3(CC(=C)C(=O)O3)c3ccccc31)c1ccccc12] |
| P14 | 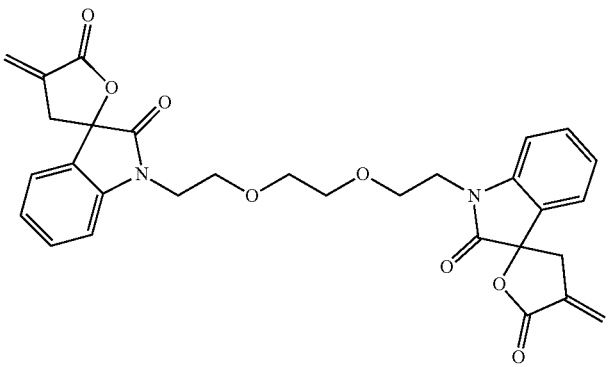 |
| P15 | 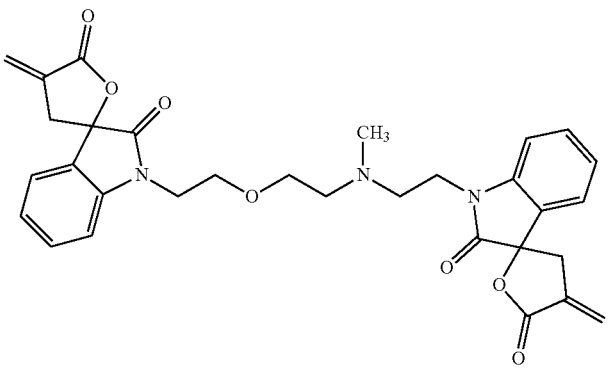 |
| P16 | 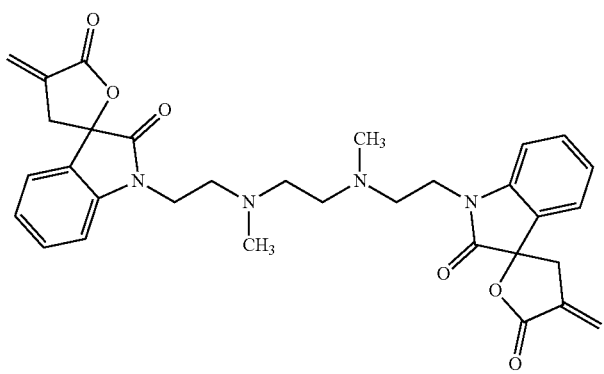 |

TABLE 1-continued

| Compound # | Structure |
|---|---|
| P17 | (structure: bis-spiroindolinone linked by -(CH₂)₂-) |
| P18 | (structure: bis-spiroindolinone linked by -(CH₂)₃-) |
| 40-038 | (structure: bis-spiroindolinone linked by -(CH₂)₄-) |
| P19 | (structure: bis-spiroindolinone linked by -(CH₂)₅-) |
| P20 | (structure: bis-spiroindolinone linked by -(CH₂)₆-) |
| P21 | (structure: bis-spiroindolinone linked by -(CH₂)₇-) |

TABLE 1-continued
| Compound # | Structure |
|---|---|
| P22 | 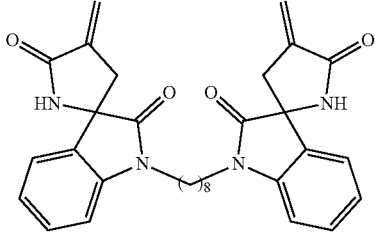 |
| P23 | 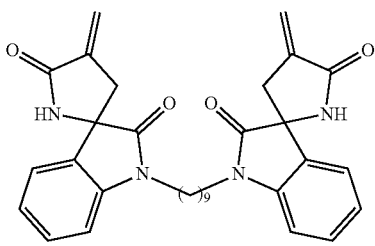 |
| P24 | 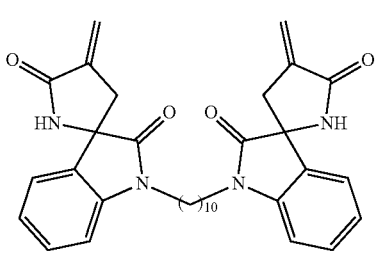 |
| P25 | 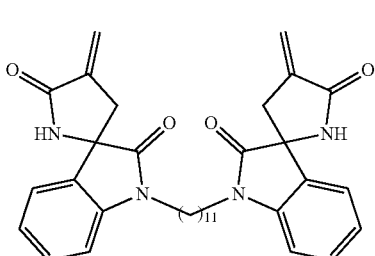 |
| P26 | 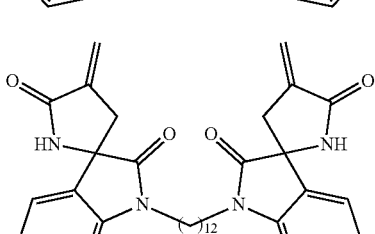 |
| P27 | 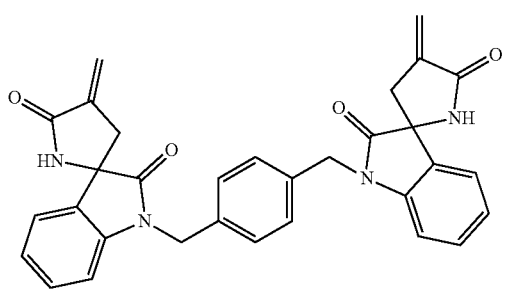 [SMILES: C=C1CC2(NC1=O)C(=O)N(Cc1ccc(CN3C(=O)C4(CC(=C)C(=O)N4)c4ccccc43)cc1)c1ccccc12] |

TABLE 1-continued

| Compound # | Structure |
|---|---|
| P28 | 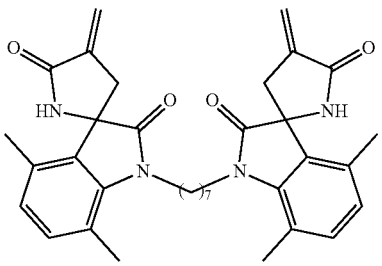 |
| | or |
| P29 | 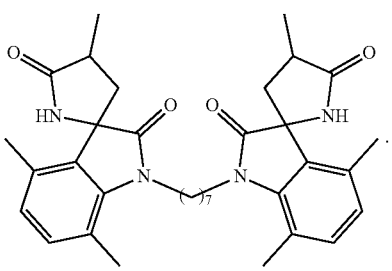 |

18. A method of treating a disease or disorder capable of being modulated by NFκB pathway inhibition, comprising administering to a subject in need thereof a therapeutically effective amount of the compound or salt of claim 1.

19. The method of claim 18, wherein the disease or disorder is selected from the group consisting of cancer, autoimmune diseases, inflammatory diseases, diabetes, cardiovascular diseases, and neurological diseases.

20. The compound or salt of claim 17, wherein the compound is compound 36-252:

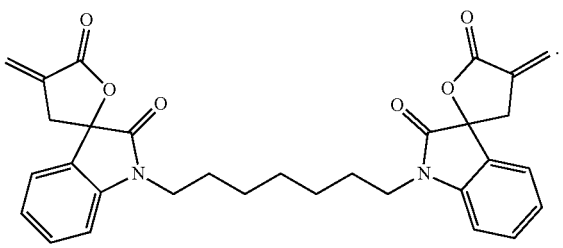

* * * * *